United States Patent
Zeng et al.

(10) Patent No.: US 10,858,744 B2
(45) Date of Patent: Dec. 8, 2020

(54) OZONE GENERATORS, METHODS OF MAKING OZONE GENERATORS, AND METHODS OF GENERATING OZONE

(71) Applicant: Advanced Diamond Technologies, Inc., Romeoville, IL (US)

(72) Inventors: Hongjun Zeng, Naperville, IL (US); Donato M. Ceres, Chicago, IL (US); John Wagner, Hawthorn Woods, IL (US)

(73) Assignee: Advanced Diamond Technologies, Inc., Romeoville, IL (US)

( * ) Notice: Subject to any disclaimer, the term of this patent is extended or adjusted under 35 U.S.C. 154(b) by 443 days.

(21) Appl. No.: 15/789,289

(22) Filed: Oct. 20, 2017

(65) Prior Publication Data
US 2018/0112317 A1    Apr. 26, 2018

Related U.S. Application Data

(60) Provisional application No. 62/410,474, filed on Oct. 20, 2016.

(51) Int. Cl.
*C25B 1/13*     (2006.01)
*C01B 13/11*    (2006.01)
(Continued)

(52) U.S. Cl.
CPC ............... *C25B 1/13* (2013.01); *C01B 13/11* (2013.01); *C01B 13/115* (2013.01);
(Continued)

(58) Field of Classification Search
None
See application file for complete search history.

(56) References Cited

U.S. PATENT DOCUMENTS 3,616,355 A    10/1971   Themy et al.
4,255,246 A    3/1981    Davis et al.
(Continued)

FOREIGN PATENT DOCUMENTS

EP    1 505 038 A2    2/2005
EP    3 202 955 A1    8/2017
(Continued)

OTHER PUBLICATIONS

PCT Notification of Transmittal of the International Search Report and the Written Opinion of the International Searching Authority, or the Declaration with accompanying PCT International Search Report and PCT Written Opinion of the International Searching Authority dated Jan. 8, 2018.

(Continued)

*Primary Examiner* — Kishor Mayekar
(74) *Attorney, Agent, or Firm* — Locke Lord LLP; Peter J. Fallon

(57) ABSTRACT

An electrolytic ozone generator includes an anode with a longitudinal edge, a cathode with a longitudinal edge spaced apart from the cathode, and an isolator. The isolator electrically separates the cathode from the anode and is semi-impermeable. The anode and cathode are impermeable for generating ozone in a flow area fluidly coupling longitudinal edges of the anode and the cathode. Ozone water apparatus, methods of making electrolytic ozone generators, and methods of generating ozone using electrolytic ozone generators are also described.

16 Claims, 18 Drawing Sheets

(51) Int. Cl.
  *C25B 11/12* (2006.01)
  *C02F 1/467* (2006.01)
  *C25B 9/08* (2006.01)
  *C02F 1/461* (2006.01)
  *A61L 2/20* (2006.01)
  *C02F 1/78* (2006.01)

(52) U.S. Cl.
  CPC .............. *C02F 1/4672* (2013.01); *C25B 9/08* (2013.01); *C25B 11/12* (2013.01); *A61L 2/202* (2013.01); *C01B 2201/12* (2013.01); *C02F 1/78* (2013.01); *C02F 2001/46147* (2013.01); *C02F 2201/4613* (2013.01); *C02F 2201/46115* (2013.01)

(56) References Cited

U.S. PATENT DOCUMENTS

| | | | |
|---|---|---|---|
| 4,401,544 | A | 8/1983 | Seto et al. |
| 4,767,511 | A | 8/1988 | Aragon |
| 4,978,438 | A | 12/1990 | Shimamune et al. |
| 5,900,127 | A | 5/1999 | Iida et al. |
| 6,319,390 | B1 | 11/2001 | Kono et al. |
| 6,855,242 | B1 | 2/2005 | Comninellis et al. |
| 7,311,977 | B2 | 12/2007 | Yokota et al. |
| 7,704,353 | B2 | 4/2010 | Stadelmann et al. |
| 7,887,679 | B2 | 2/2011 | Kitaori et al. |
| 7,951,274 | B2 | 5/2011 | Yoshida et al. |
| 8,277,623 | B2 | 10/2012 | Kato et al. |
| 8,323,461 | B2 | 12/2012 | Scarsbrook |
| 8,361,289 | B2 | 1/2013 | Whitehead et al. |
| 8,431,006 | B2 | 4/2013 | Arihara et al. |
| 8,591,856 | B2 | 11/2013 | Doering et al. |
| 8,734,626 | B2 | 5/2014 | Arihara et al. |
| 8,815,064 | B2 | 8/2014 | Kato et al. |
| 8,980,079 | B2 | 3/2015 | Yost, III et al. |
| 9,380,920 | B2 | 7/2016 | Pollack |
| 2002/0130091 | A1 | 9/2002 | Ekberg et al. |
| 2005/0139487 | A1 | 6/2005 | Zwicker et al. |
| 2008/0251108 | A1 | 10/2008 | Nagai et al. |
| 2009/0211918 | A1 | 8/2009 | Hardee |
| 2009/0324810 | A1 | 12/2009 | Serikawa et al. |
| 2010/0006450 | A1 | 1/2010 | Whitehead et al. |
| 2010/0135869 | A1 | 6/2010 | Shiue et al. |
| 2010/0170783 | A1 | 7/2010 | Wesner et al. |
| 2012/0138478 | A1* | 6/2012 | Yost, III ............... C25B 9/04 205/626 |
| 2012/0205255 | A1 | 8/2012 | Roster et al. |
| 2013/0032491 | A1 | 2/2013 | Nitta et al. |
| 2013/0206604 | A1 | 8/2013 | Lutz et al. |
| 2013/0206654 | A1 | 8/2013 | Lutz et al. |
| 2013/0240458 | A1 | 9/2013 | Conradt et al. |
| 2013/0341204 | A1 | 12/2013 | Sung |
| 2014/0174942 | A1 | 1/2014 | Wylie et al. |
| 2014/0054166 | A1 | 2/2014 | Brandon et al. |
| 2014/0076724 | A1 | 3/2014 | Cheng et al. |
| 2015/0129419 | A1 | 5/2015 | Sekiguchi et al. |
| 2015/0167183 | A1 | 6/2015 | Müller et al. |
| 2015/0376804 | A1 | 12/2015 | Gorokhovsky et al. |
| 2016/0101997 | A1 | 4/2016 | Hamaguchi et al. |

FOREIGN PATENT DOCUMENTS

| | | |
|---|---|---|
| GB | 2490913 A | 11/2012 |
| WO | WO 02/17975 A1 | 3/2002 |
| WO | WO 2011/135749 A1 | 11/2011 |
| WO | WO 2014/141587 A1 | 9/2014 |

OTHER PUBLICATIONS

Marshall Stoneham, "Forward," pp. ix-x (Jun. 2000).
D.M. Gruen, "Applications of ultrananocrystalline diamond films," pp. 313-317 (Jan. 2000).
M.H. Nazaré et al., Properties, Growth and Applications of Diamond, pp. xi-xx (Dec. 8, 2000).
S. Ferro et al., "Chlorine Evolution at Highly Boron-Doped Diamond Electrodes," Journal of The Electrochemical Society, 147:7, pp. 2614-2619 (2000).
International Preliminary Report on Patentability for PCT Application No. PCT/US2017/057645, dated Apr. 23, 2019.
Chaplin, Brian P et al., "Characterization of performance and failure mechanisms of boron-doped ultrananocrystalline diamond electrodes" J Appl Electrochem (2011) 41:1329-1340.
Extended European search report dated May 26, 2020 corresponding to Application No. 17862896.2.
Supplementary European search report dated Jun. 15, 2020 corresponding to Application No. 17862896.2.

* cited by examiner

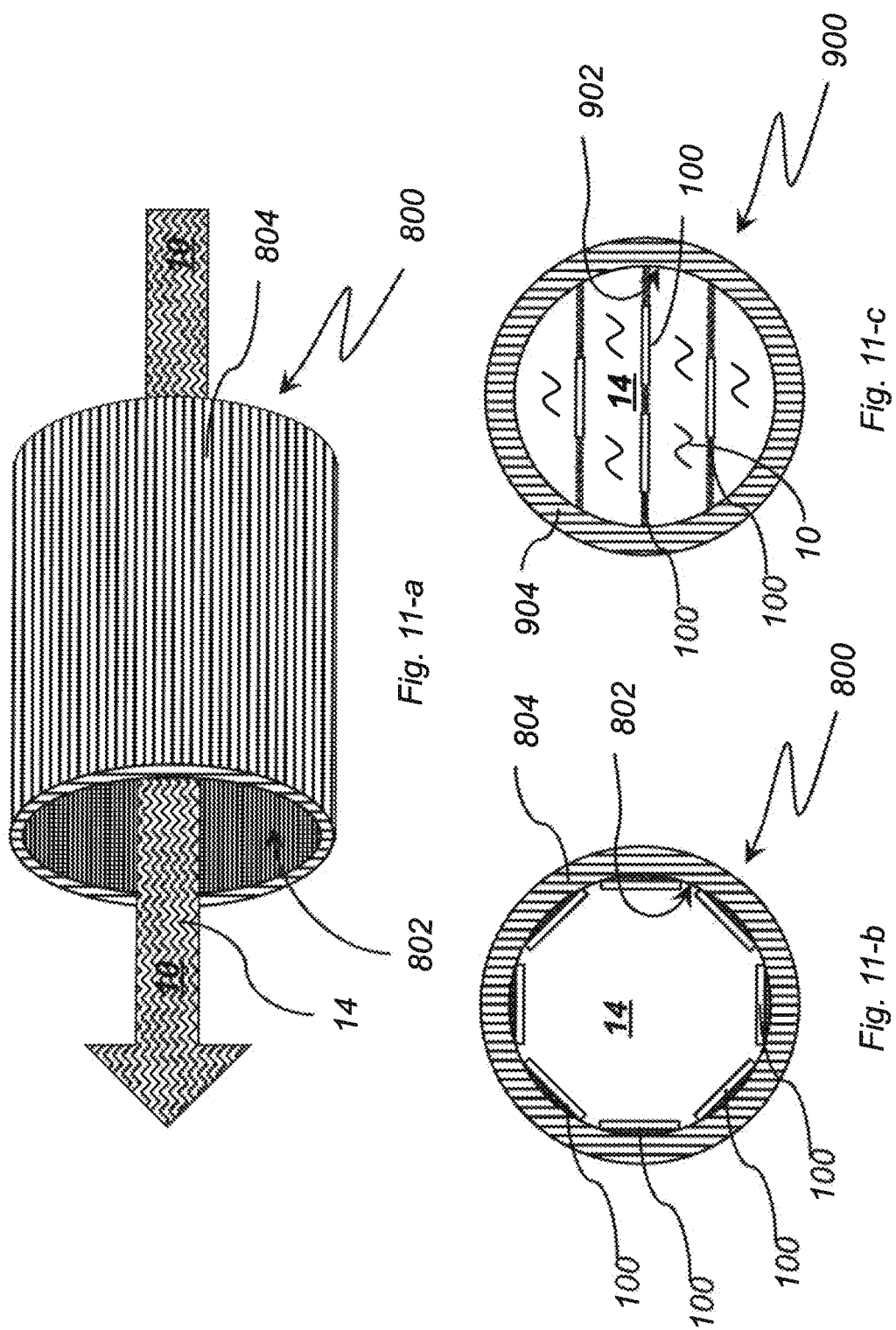

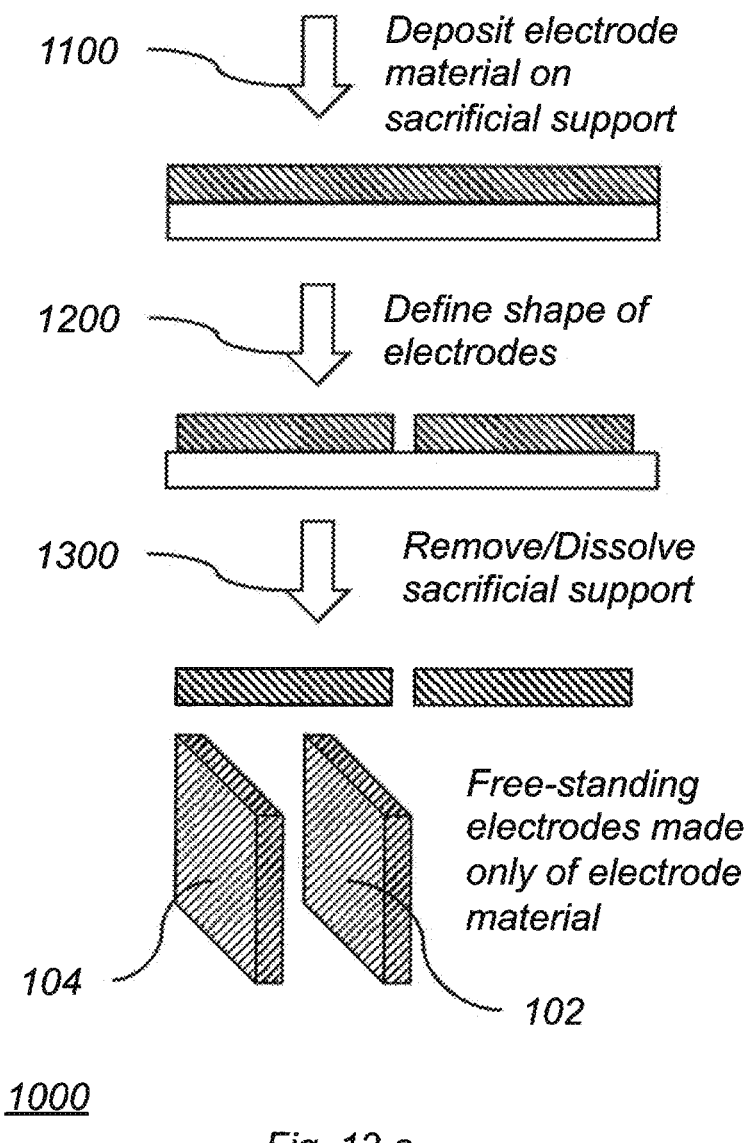
Fig. 12-a

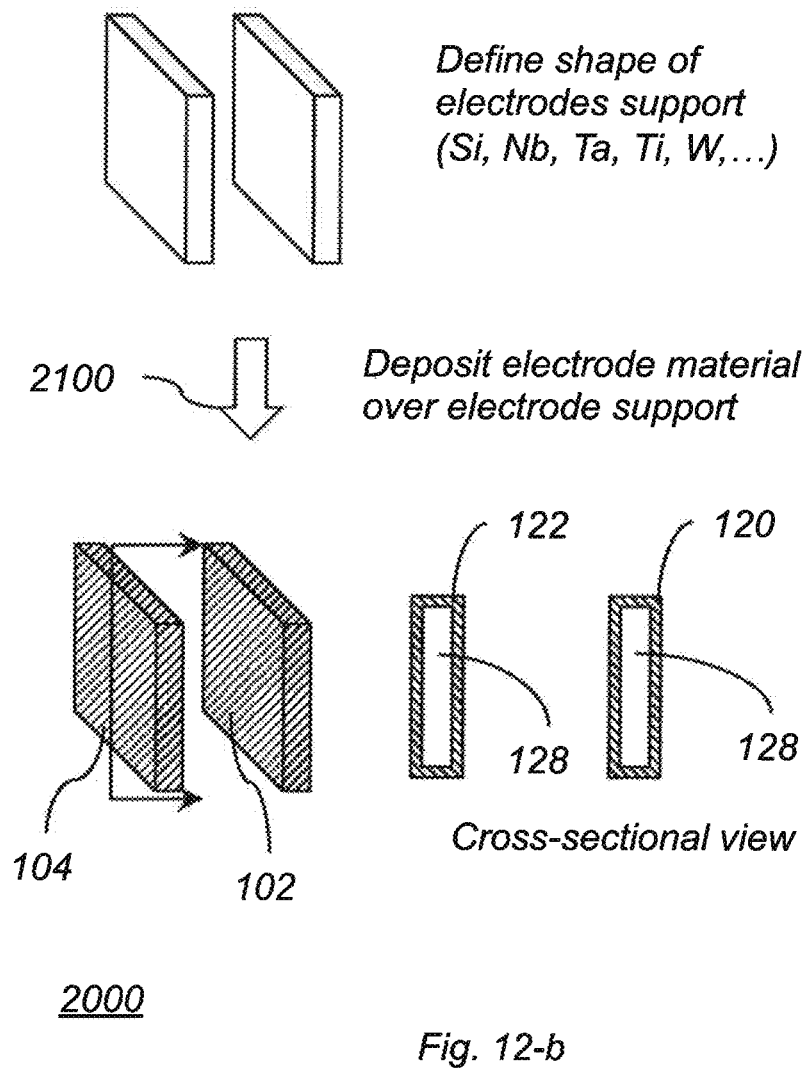
Fig. 12-b

US 10,858,744 B2

OZONE GENERATORS, METHODS OF MAKING OZONE GENERATORS, AND METHODS OF GENERATING OZONE

CROSS-REFERENCE TO RELATED APPLICATION

This application claims the benefit of priority under 35 U.S.C. § 119(e) to U.S. Provisional Application No. 62/410,474, filed Oct. 20, 2016, the contents of which are incorporated by reference herein in their entirety.

BACKGROUND OF THE INVENTION

1. Field of the Invention

The present disclosure relates to ozone generation, and more particularly to electrolytic ozone generators and methods of generating ozone with electrolytic ozone generators.

2. Description of Related Art

Ozone is a molecule with high oxidation potential commonly used in various applications such as the treatment of wastewater, hard surface sanitation and disinfection, as well as for extending the shelf life of perishable produce and other food items. Ozone is a gas, and while for some applications the use of ozone in the gas form is preferred, ozone dissolved in water (ozone water) has particular advantages. Most notably, the presence of the ozone in the air is strictly regulated by governmental agencies, while ozone water has no particular limitations, except for drinking water. However, since the lifetime of ozone is reasonably short (in the range of tens of minutes, depending on the water conditions), ozone does not leave any residual contaminant—and the EPA and FDA therefore allow the use of ozone on produce, meat, and poultry.

Ozone is generally produced by corona or plasma discharge in air or a pure oxygen atmosphere or by the electrochemical dissociation of liquid water molecules. In non-electrochemical processes, in order to achieve complete dissolution of ozone in the water, ozone generating systems require additional components such as (Venturi injectors, gas contactors pumps, etc.) that significant increase the complexity and costs of the equipment. The dissolution of ozone gas in water is significantly less efficient in applications with low water flow rates (such as in residential settings), potentially causing the ozone provided in the generator to outgas from the water and into the surrounding environment—potentially exceeding the regulatory limits for ozone and/or creating a hazard. Ozone generation by water electrolysis is particularly more suitable when the application requires low flow rates and a small footprint at the point of use. Since electrolytic ozone generation utilizes solely the oxygen of the liquid water, it does not require additional oxygen feeds and results in significantly simpler device and results is less ozone outgassing into the surrounding environment.

Ozone generation by electrochemical dissociation of liquid water molecules typically employs a cathode and anode electrode pressed into close contact with a proton exchange membrane (PEM). Since the electrochemical reactions take place at a rate most favorable to ozone generation on the portion of the electrode that is in contact with the membrane and closest to the counter-electrode at the electrode-membrane interface (hereafter referred to as the electrode-membrane interface), the anode and cathode electrodes typically are porous to allow the liquid water molecules to reach the respective electrode surfaces, examples including solid structures having holes or slots that allow the water to reach the membrane interface.

Within these interfacial electro-active regions, water electrolysis occurs at the anode as described by the following equations:

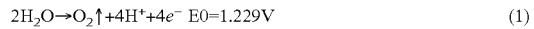

$$2H_2O \rightarrow O_2\uparrow + 4H^+ + 4e^-\ \ E0=1.229V \quad (1)$$

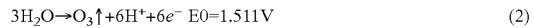

$$3H_2O \rightarrow O_3\uparrow + 6H^+ + 6e^-\ \ E0=1.511V \quad (2)$$

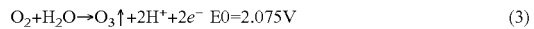

$$O_2 + H_2O \rightarrow O_3\uparrow + 2H^+ + 2e^-\ \ E0=2.075V \quad (3)$$

As the water is electrolyzed at the anode by oxidation, the resulting protons are transferred through the PEM to the cathode where they evolve to hydrogen gas, as described by the following equations:

$$2H^+ + 2e^- \rightarrow H_2\uparrow\ \ E0=0.000V \quad (4)$$

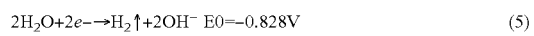

$$2H_2O + 2e^- \rightarrow H_2\uparrow + 2OH^-\ \ E0=-0.828V \quad (5)$$

The symbol ($\uparrow$) indicates that the species formed is in the gaseous form.

The presence of the PEM is very important for the electrolytic formation of ozone as it efficiently transfers the protons from the anode to the cathode. The ozone gas generated by electrolysis is well dissolved in the water and does not outgas in absence of agitation. The trace amount of gas bubbles formed at the anode and cathode, namely oxygen and hydrogen gas, respectively, however, can hinder the water access to re-hydrate the electroactive regions and needs to leave the holes in order to allow the reactions (1)-(5) to continue. Because of this important electrochemical requirement, several patents have investigated a variety of electrode designs to optimize the water access to the interface as well as the gas removal that is generated.

In the case of solid electrodes comprising of a plurality of holes, one can understand that the ozone production is related to the number of holes present on the electrode. Since the electrochemical reactions and the gas removal occur at best possible rate at the electrode-membrane interface, the greater the number of through holes and the larger the area is at the electrode-membrane interface, the more ozone could be generated. However, increasing the number of through holes can have a detrimental effect on the operation of the device. In particular, the structural stability of the electrode can be severely affected. Since anode and cathode are pressed against the PEM, the compression can potentially deform or even break the electrode. Moreover, since the complex through-hole shapes are manufactured using standard machining techniques (such as water jet), the fabrication cost electrodes with through-holes can be high. And the shape of the through-holes can themselves make it difficult for the gases to evacuate the holes once generated.

Such conventional systems and methods have generally been considered satisfactory for their intended purpose. However, there is still a need in the art for improved electrolytic ozone generators, methods of making electrolytic ozone generators, and methods of generating ozone using electrolytic ozone generators. The present disclosure provides a solution for this need.

SUMMARY OF THE INVENTION

An electrolytic ozone generator includes an anode with a longitudinal edge, a cathode with a longitudinal edge spaced apart from the cathode, and a semi-permeable isolator. The cathode and the anode are impermeable to water for generating ozone in a flow area fluidly coupling the longitudinal edge of the anode with the longitudinal edge of the cathode.

In certain embodiments the anode can include an electrically conductive material. The cathode can include an electrically conductive material. The anode and the cathode can include a common material. The material forming the anode and/or the cathode can include diamond. The material forming the anode and/or the cathode can include at least of boron-doped diamond, nitrogen-doped diamond, and phosphorus-doped diamond. The anode and cathode can define a non-linear profile. The anode and cathode can define a linear longitudinal axis. The anode and cathode can define a non-linear longitudinal axis. Either (or both) the anode and the cathode can have a rectangular profile. Either (or both) the anode and the cathode can have an arcuate profile.

In accordance with certain embodiments, the electrolytic ozone generator can include a support. The support can be an internal support. The material forming the anode can be deposited over the internal support. The material forming the cathode can be deposited over the internal support. The support can be an external support. The anode can be assembled to a surface of the external support. The anode can be deposited to the surface of the external support. The cathode can be assembled to the surface of the external support. The cathode can be deposited over the surface of the external support. The internal support can include silicon, niobium, tantalum, and tungsten. The external support can include a segment of a silicon wafer.

It is contemplated that the isolator can be fixed to the surface of the external support between the anode and the cathode. The isolator can include a proton exchange membrane. The isolator can include a solid polymer electrolyte. The isolator can be connected to the external support. The electrolytic ozone generator can include a plurality of isolators. An intermediate isolator can electrically separate first electrode pair from a second electrode pair. The intermediate isolator can be arranged on a side of the anode of the first anode pair opposite the cathode of the second electrode pair. The isolator can limit ozone generation to an active area extending along the longitudinal edge of one or more of the anode and cathode by promoting proton transfer from the anode to the cathode.

It is also contemplated that, in accordance with certain embodiments, the electrolytic ozone generator can include a positive lead. The positive lead can be electrically connected to the anode. The electrolytic ozone generator can include a negative lead. The negative lead can be electrically connected to the cathode. A power source can be connected to the anode and the cathode through the positive lead and the negative lead. The power source can include a variable frequency power source. The power source can include a reversing polarity power source with variable frequency of reversing polarity.

An ozone water generator can include a water conduit defining a flow area and an electrolytic ozone generator as described above. The electrolytic ozone generator is fixed to an interior surface of the water conduit such that the flow area fluidly couples the longitudinal edge of the anode to the longitudinal edge of the cathode in a common space.

In certain embodiments the common space can be located on a single side of the electrolytic ozone generator. In accordance with certain embodiments, the common space is a first common space and the flow area can fluidly couple a longitudinal edge of the anode to a longitudinal edge of the cathode in a second common space on a side of the electrolytic ozone generator opposite the first common space.

A method of making ozone water includes applying a positive voltage to an anode with a longitudinal edge and applying a negative voltage to a cathode with a longitudinal edge spaced apart from the anode. A semi-permeable isolator electrically separating the anode from the cathode is wetted with water flowing over the anode and the cathode. Ozone is generated in a common flow area fluidly coupling the longitudinal edge of the anode with the longitudinal edge of the cathode without flowing water through the anode, cathode, and isolator.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein:

FIGS. 11a-11c are a side elevation and cross-sectional views of exemplary ozone water apparatus, showing the electrolytic ozone generators arranged on the interior surface of a water conduit and within the flow area of the water conduit, respectively;

FIGS. 12a-12b are diagrams of methods of making the anodes and cathodes of the electrolytic ozone generators, showing the self-support anodes and cathodes and internally supported anode and cathodes, respectively;

DETAILED DESCRIPTION OF THE PREFERRED EMBODIMENTS

Figure 1:
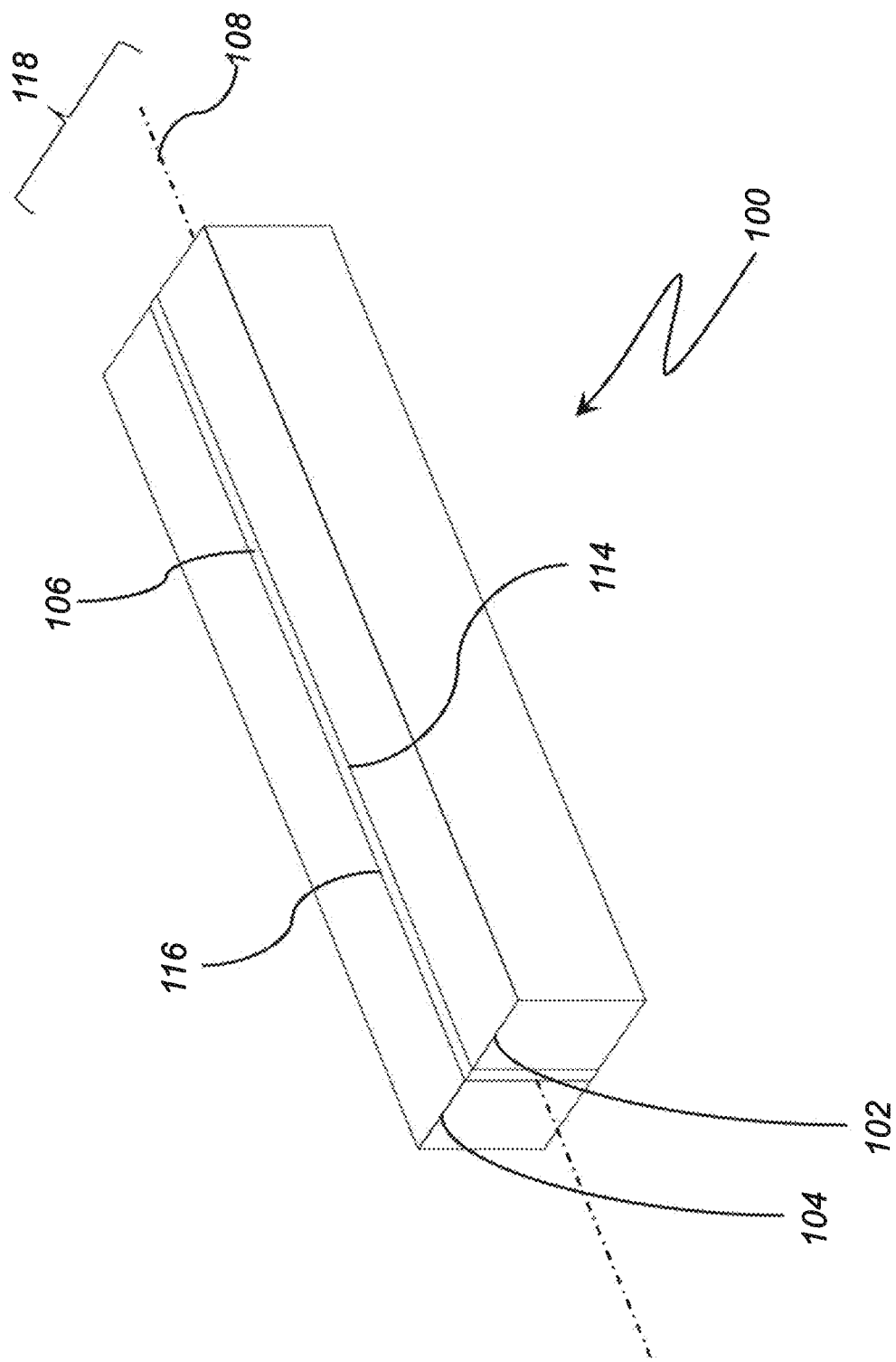
FIG. 1 is a perspective view of an electrolytic ozone generator, schematically showing an anode separated from a cathode by an isolator in an electrode pair.

Reference will now be made to the drawings wherein like reference numerals identify similar structural features or aspects of the subject disclosure. For purposes of explanation and illustration, and not limitation, a partial view of an exemplary embodiment of an electrolytic ozone generator in accordance with the disclosure is shown in FIG. 1 and is designated generally by reference character 100. Other embodiments of electrolytic ozone generators, methods of making electrolytic ozone generators, and methods of making ozone water using electrolytic ozone generators in accordance with the disclosure, or aspects thereof, are provided in FIGS. 2-17, as will be described. The apparatus and methods described herein can be used for adding dissolved ozone to water, such as in purification devices, though the present disclosure is not limited to purification devices or to applications requiring dissolved ozone in general.

Referring to FIG. 1, electrolytic ozone generator 100 is shown. Electrolytic ozone generator 100 includes an anode 102, a cathode 104, and an isolator 106. Anode 102 has a longitudinal 114 that spaced apart from a longitudinal edge 116 of cathode 104 by isolator 106. Isolator 106 electrically separates cathode 104 from anode 102 and is semi-permeable. Anode 102 and cathode 104 are impermeable to water for generating ozone in a flow area 101 (shown in FIG. 4) fluidly coupling longitudinal edge 114 of anode 102 and longitudinal edge 116 of cathode 104. As used herein, the term semi-permeable means that water can permeate the material but does not readily flow through the structure formed by the material.

Isolator 106 is arranged between anode 102 and cathode 104, defines a longitudinal axis 108 extending along the length of electrolytic ozone generator 100, and has an anode face and a laterally opposite cathode face. Anode 102 is connected to the anode face of isolator 106 such that an anode longitudinal edge 114 extends along the interface of anode 102 and isolator 106. Cathode 104 is connected to the cathode face of isolator 106 such that a cathode longitudinal edge 116 extends along the interface of cathode 104 and isolator 106, cathode 104 arranged on side of isolator 106 laterally opposite anode 102. It is contemplated that isolator 106 fix cathode 104 to anode 102 to form an electrode pair 118. Although shown as a linear axis 108, it is to be understood and appreciated anode pair 118 can define a non-linear longitudinal axis 108, such as a curved axis, as suited for an intended application. Further, although illustrated as having rectangular profiles, either or both of anode 102 and cathode 104 can have an arcuate profile, as suited for an intended application.

As will be appreciated by those of skill in the art, conventional electrolytic ozone generating generally have only two electrodes with holes or slots. The two electrodes are typically assembled in a way that the water needs to access the membrane electrode interface inside the hole, the membrane thereby preventing the water to readily pass through the electrode stack. This typically prevents stacking additional electrodes to provide additional ozone-producing areas, thereby limiting ozone output absent increasing the number of holes (which decreases their mechanical stability) or by multiplying the number of cells (which has a number of disadvantages such as increased pressure drop, increased cost and complexity).

In the illustrated exemplary embodiment of electrolytic ozone generator 100, electrode pair 118 has no holes. Generation of ozone gas 142 (shown in FIG. 4) takes place externally of the electrode pair 118. External generation allows for increasing ozone-producing area as additional electrode pairs can be added, e.g., one or more second electrode pair 218 (shown in FIG. 2), thereby increasing ozone output a electrolytic ozone generator 100 relative to conventional electrolytic ozone generators without reducing the mechanical stability of the structure of electrolytic ozone generator 100, as would be required in a membrane-type ozone generator.

Figure 2:
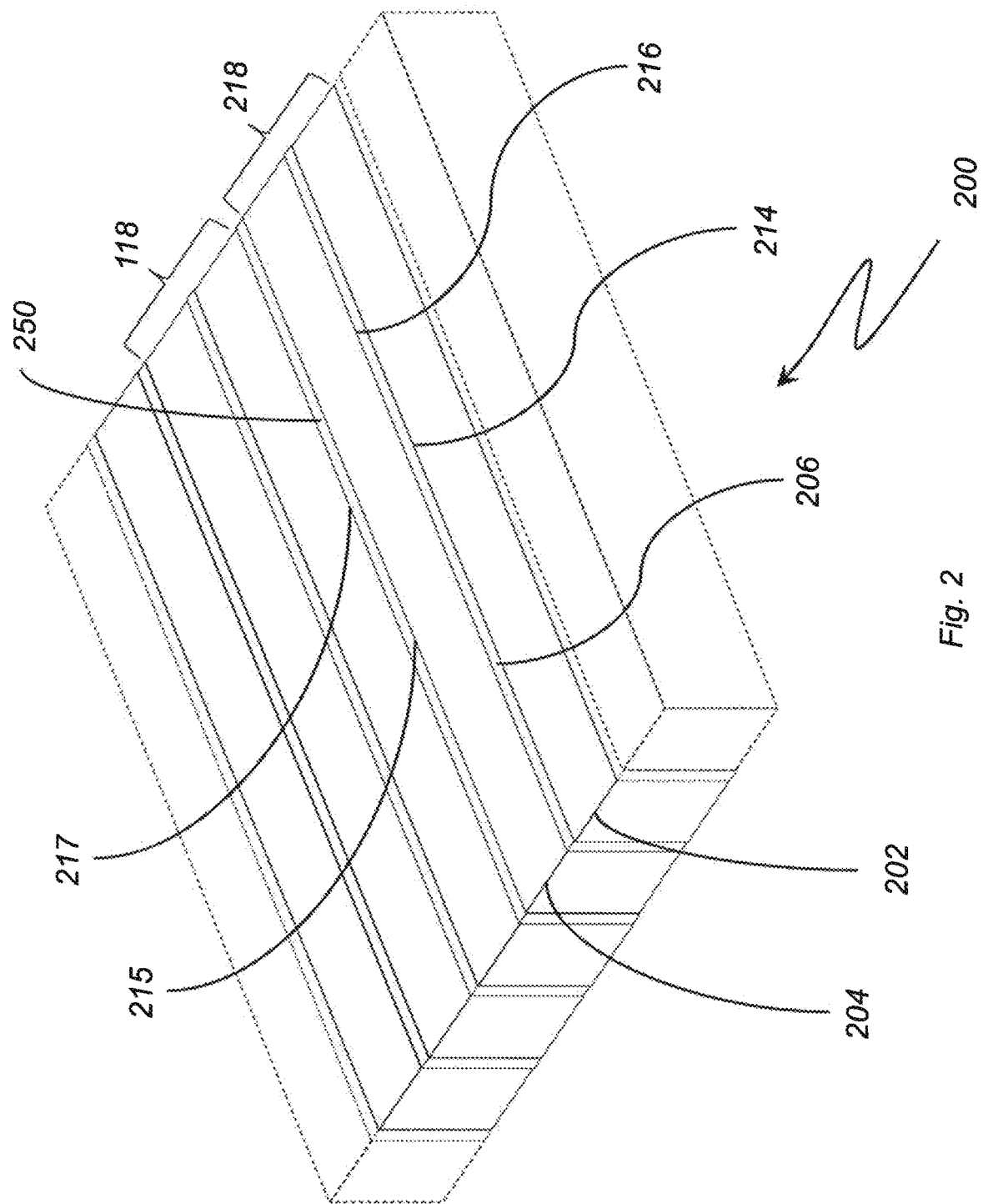
FIG. 2 is a perspective view of an electrolytic ozone generator including the electrode of FIG. 1, shown a plurality of electrode pairs separated by intermediate isolators.

With reference to FIG. 2, an electrolytic ozone generator 200 is shown. Electrolytic ozone generator 200 is similar to electrolytic ozone generator 100 (shown in FIG. 1) and additionally includes at least one second electrode pair 218. Second electrode pair 218 is similar to first electrode pair 118 and includes a anode 202, an cathode 204, and an isolator 206. Isolator 206 is arranged between anode 202 and cathode 204 and has an anode face and a laterally opposite cathode face. Anode 202 is connected to the anode face such that an anode longitudinal edge 214 extends along the interface of anode 202 and isolator 206. Cathode 204 is connected to the cathode face of isolator 206 such that a cathode longitudinal edge 216 extends along the interface of cathode 204 and isolator 206, cathode 204 being arranged on side of isolator 206 laterally opposite anode 202, isolator 206 fixing cathode 204 to anode 202 to form second electrode pair 218.

Figure 4:
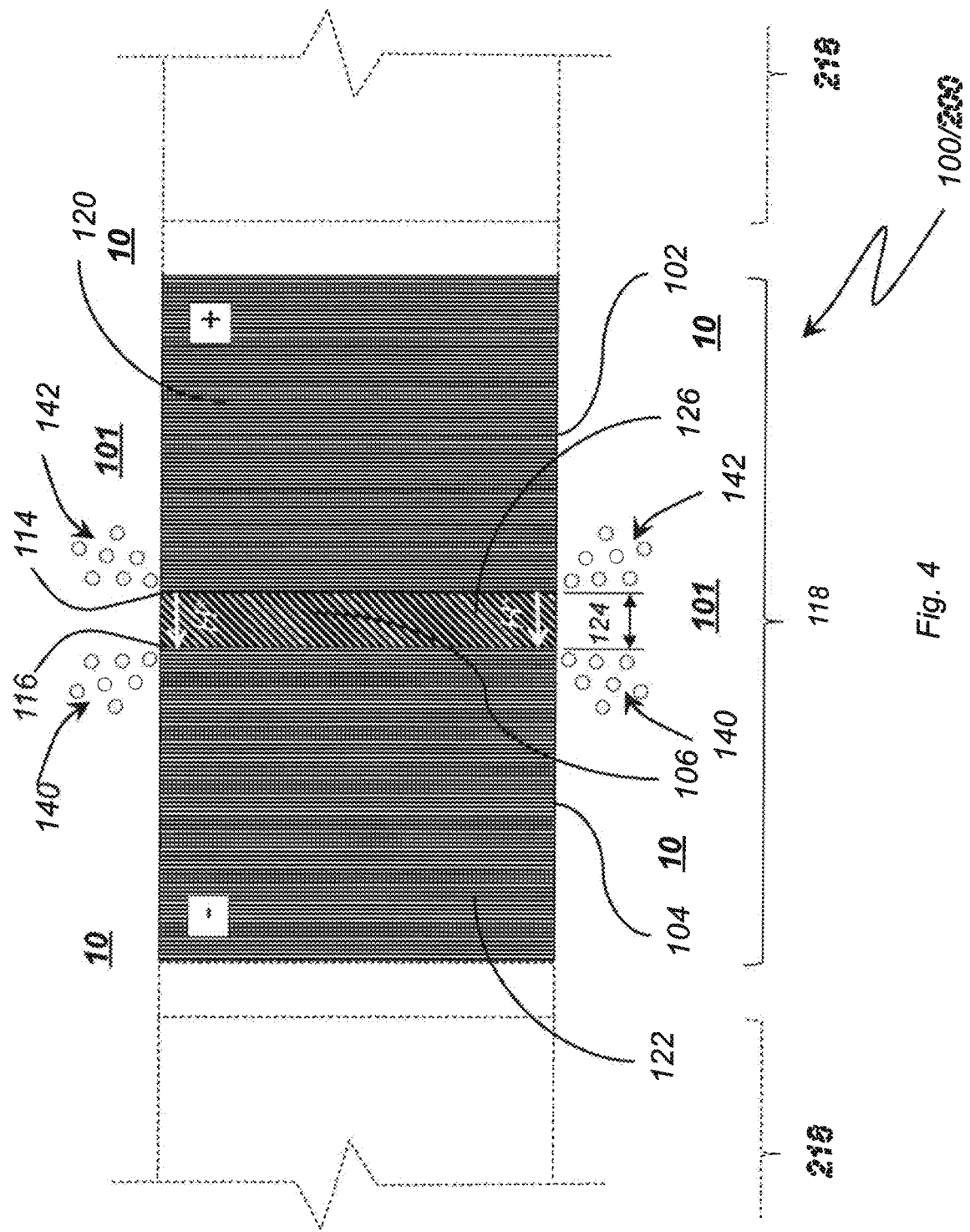
FIGS. 4 and 5 are cross-sectional views of the electrolytic ozone generator of FIGS. 1 and 2, showing self-supporting electrodes and electrodes with internal support structures, respectively.

An intermediate isolator 250 is arranged between cathode 104 and anode 202. Intermediate isolator 250 is similar to isolator 106 and isolator 206, intermediate isolator 250 providing electrical separation between anode 102 and cathode 204 as well as coupling second electrode pair 218 to first electrode pair 118. As will be appreciated by those of skill in the art in view of the present disclosure, coupling one or more second electrode pair 218 to first electrode pair 118 increases the active area of electrolytic ozone generator 200 in relation to electrolytic ozone generator 100 (shown in FIG. 1). In particular, second electrode pair 218 provides an additional anode longitudinal edge 214 and cathode longitudinal edge 216 for evolving additional ozone gas 142 from water 10 (as shown in FIG. 4), increasing output of ozone water from electrolytic ozone generator 200. As will also be appreciated by those of skill in the art, the illustrated arrangement is scalable, additional electrode pairs being connected to electrode pair 118 by additional intermediate isolators. In the illustrated exemplary embodiment three (3) electrode pairs are shown. This is for illustration purposes only as electrolytic ozone generator 200 can have two (2)

electrode pairs or more than three (3) electrode pairs, as suitable for an intended application.

Figure 3:
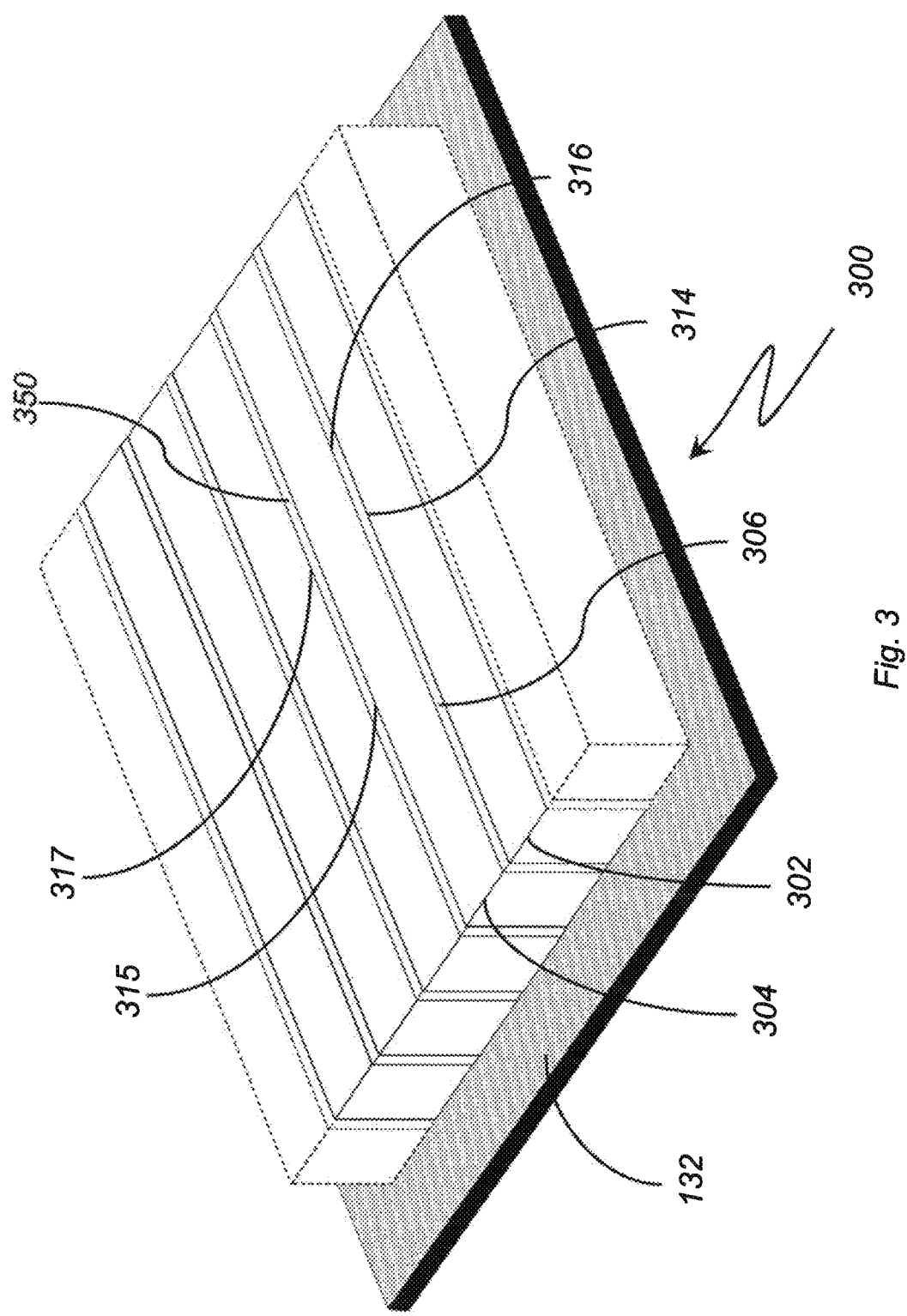
FIG. 3 is a perspective view of an electrolytic ozone generator, showing a plurality of electrode pairs separated by intermediate isolators arranged on an external support.

With reference to FIG. 3, an electrolytic ozone generator 300 is shown. Electrolytic ozone generator 300 is similar to electrolytic ozone generator 100 (shown in FIG. 1) and additionally includes an external support 132. External support 132 is arranged on a side of anode 102 and cathode 104 opposite longitudinal edge 114 and longitudinal edge 116 to provide mechanical support to electrode pair 118. External support 132 additionally provides a structure for fixing, with electrical isolation, electrode pair 118 to an interior surface 802 (shown in FIG. 11b) of a water conduit 804 (shown in FIG. 11b) in an ozone water apparatus 800 (shown in FIG. 11b). As will be appreciated by those of skill in the art in view of the present disclosure, this allows flow area 101 (shown in FIG. 4) to be swept by water 10 (shown in FIG. 11a) traversing water conduit 804, facilitating incorporation of ozone into water 10 as it is generated by electrolytic ozone generator 100.

In the illustrated exemplary embodiment electrolytic ozone generator 300 includes a plurality of electrode pairs interconnected by intermediate isolators, e.g., intermediate isolator 350. Intermediate isolator 350 is similar to isolator 106 and separates the anode and cathode of the respective adjacent anode pairs. The separation allows for additional ozone generation at longitudinal edge 317 of the anode of one electrode pair while hydrogen is evolved at the longitudinal edge 315 of the cathode of the adjacent electrode pair, increasing ozone generation of electrolytic ozone generator 300.

With reference to FIG. 4, electrolytic ozone generator 100 is shown in a lateral cross-section. Anode 102 is constructed of an anode material 120. Anode material 120 is an electrically conductive material and is connectable to a power source, e.g., power source 550 (shown in FIG. 10). It is contemplated that anode material 120 be impermeable to water 10 (shown in FIG. 4), water 10 thereby being unable to penetrate and/or traverse anode 102. In accordance with certain embodiments anode 102 is non-porous (i.e., solid) and has no flow passages extending therethrough. As will be appreciated by those of skill in the art in view of the present disclosure, such construction renders electrolytic ozone generator 100 mechanically robust. It is contemplated that anode material 120 can include a diamond material, such as a diamond film deposited on a substrate. In certain embodiments the diamond material forms the entirety of anode 102. Examples of suitable diamond material include boron-doped diamond (BDD), nitrogen-doped diamond and phosphorus-doped diamond as well as other diamond films, such as those available from Advanced Diamond Technologies Incorporated of Romeoville, Ill.

Cathode 104 is constructed of a cathode material 122. Cathode material 122 is also electrically conductive and is connectable to a power source, e.g., power source 550 (shown in FIG. 10), for developing a voltage potential difference between cathode 104 and anode 102. It is contemplated that cathode 104 be impermeable to water 10 (shown in FIG. 4), water 10 being unable to penetrate and/or traverse cathode 104. Cathode 104 can also be solid and have no flow passages extending therethrough, providing additional robustness to electrolytic ozone generator 100. In certain embodiments cathode material 122 includes a diamond material. In accordance with certain embodiments, cathode material 122 can be entirely constructed of the diamond material, such as BDD. It is contemplated that cathode material 122 can be identical to anode material 120, for example, anode 102 and cathode 104 being deposited during a common diamond film deposition operation and gap 124 being defined laterally therebetween for subsequent construction of isolator 106.

Isolator 106 includes an electrically insulating isolator material 126. Isolator material 126, and thereby isolator 106, electrically isolates anode 102 from cathode 104. It is contemplated that isolator 106 can be either permeable or impermeable according the construction of isolator 106. In this respect, in certain embodiments, isolator material 126 can include a proton exchange membrane (PEM), which provides resilience to electrolytic ozone generator 100. Examples of suitable proton exchange membranes include those constructed from Nafion and similar materials. In accordance with certain embodiments, isolator material 126 can include a solid polymer electrolyte material incorporated in a cured resin. The cured resin can be arranged in an isolator gap 124 defined between anode 102 and cathode 104, thereby providing rigidity and still further mechanical robustness to electrolytic ozone generator 100. Suitable isolator materials include Nafion® plastic membranes, available from The Chemours Company of Wilmington, Del., like Nafion HP, Nafion 211, Nafion XL, Nafion 212, Nafion 115, Nafion 117, Nafion 1110, or D520 Nafion Dispersion, D521 Nafion Dispersion, D1021 Nafion Dispersion, D2020 Nafion Dispersion, D2021 Nafion Dispersion, DE2029 Nafion Dispersion.

The electrical isolation provided by isolator 106 to anode 102 and cathode 104 enables generation of a potential difference across anode 102 and cathode 104. Upon potential difference reaching a predetermined level a flow of protons $H^+$ develops through water wet portion of insulator 106 proximate to water 10 (i.e., within isolator 106) between anode longitudinal edge 114 and cathode longitudinal edge 116, the flow of protons $H^+$ causing hydrogen gas 140 and ozone gas 142 from the electrolysis of water in proximity to anode longitudinal edge 114 and cathode longitudinal edge 116 according to equations (1)-(5) above.

As will be appreciated by those of skill in the art in view of the present disclosure, ozone gas 142, once formed, readily dissolves into water 10. The dissolved ozone gas 142 imparts into water 10 ozone oxidizing properties that render water 10 suitable various processes, such industrial laundering, floriculture, produce and other perishable food items healthcare applications, janitorial applications, etc. it is contemplated that anode longitudinal edge 114 and cathode longitudinal edge 116 be in fluid communication with one another within a common space occupied by water 10, water 10 flowing therethrough to acquire ozone gas 142 for use in a purifier apparatus. Examples of purifier apparatus contemplated include mobile disinfection units available under the Diamonox® trade name, also available from Advanced Diamond Technologies Incorporated of Romeoville, Ill.

Figure 5:
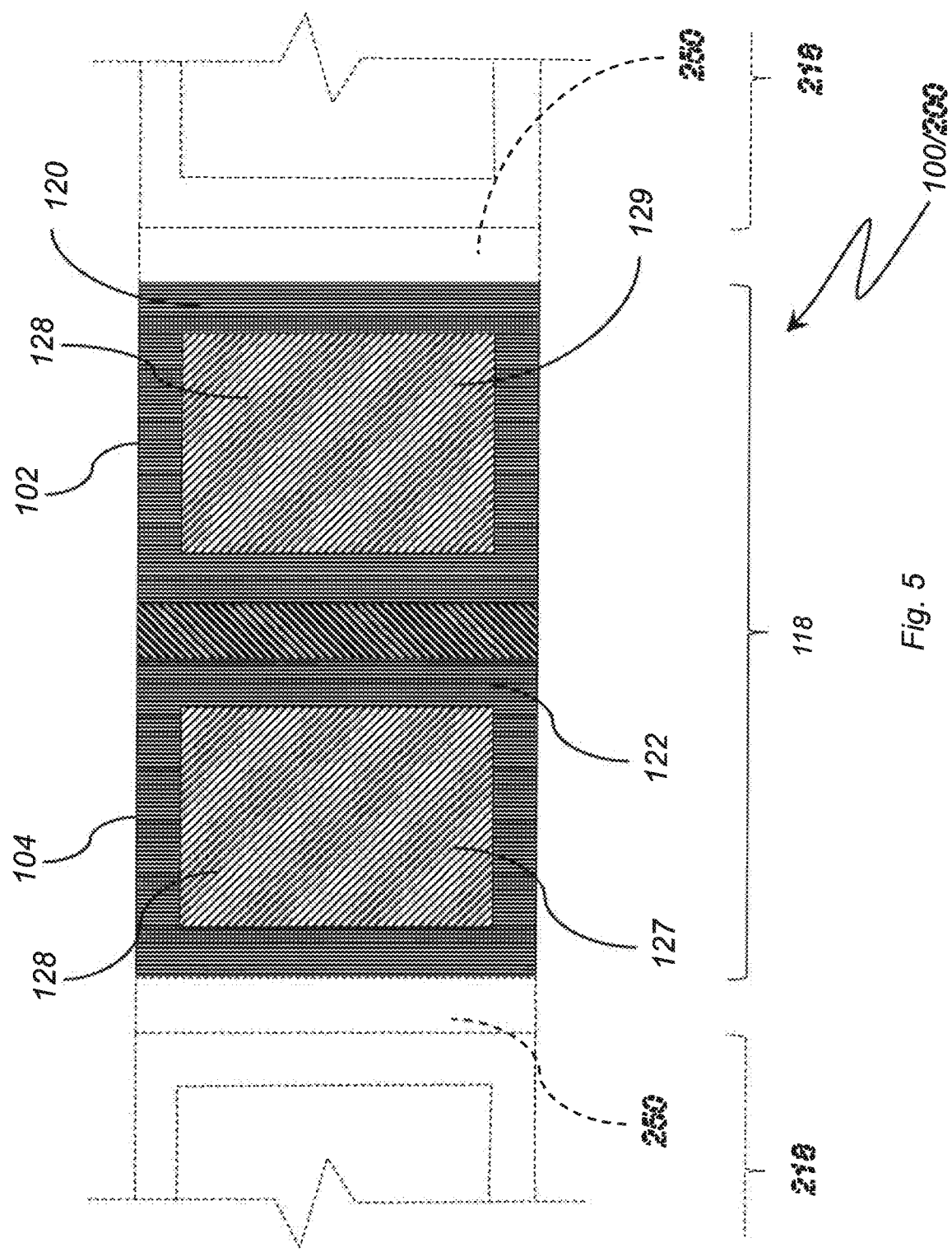

With reference to FIG. 5, electrolytic ozone generator 100 according to an embodiment having an internal support 128. In the illustrated exemplary embodiment both anode 102 and cathode 104 have a respective internal support 128. Internal support 128 includes a support material 127 which serves as a substrate from cathode material 122. Internal support 128 includes a support material 129, which similarly serves as a substrate for anode material 120. Non-limiting examples of support material 127 and/or support material 129 include silicon, niobium, tantalum, tungsten, titanium, conductive ceramics, conductive metal oxides, conductive carbides and carbon materials.

Internal support 128 renders electrode pair 118 self-supporting, and allows for use of relatively small amounts of anode material 120 and cathode material 122. This can be advantageous in applications where relatively thin layers of electrode materials are sufficient to support the electrolytic generation of ozone. It can also support the fabrication of relatively small electrode pairs, enabling the electrode pairs to be arranged as a lining in a water conduit.

Figure 6:
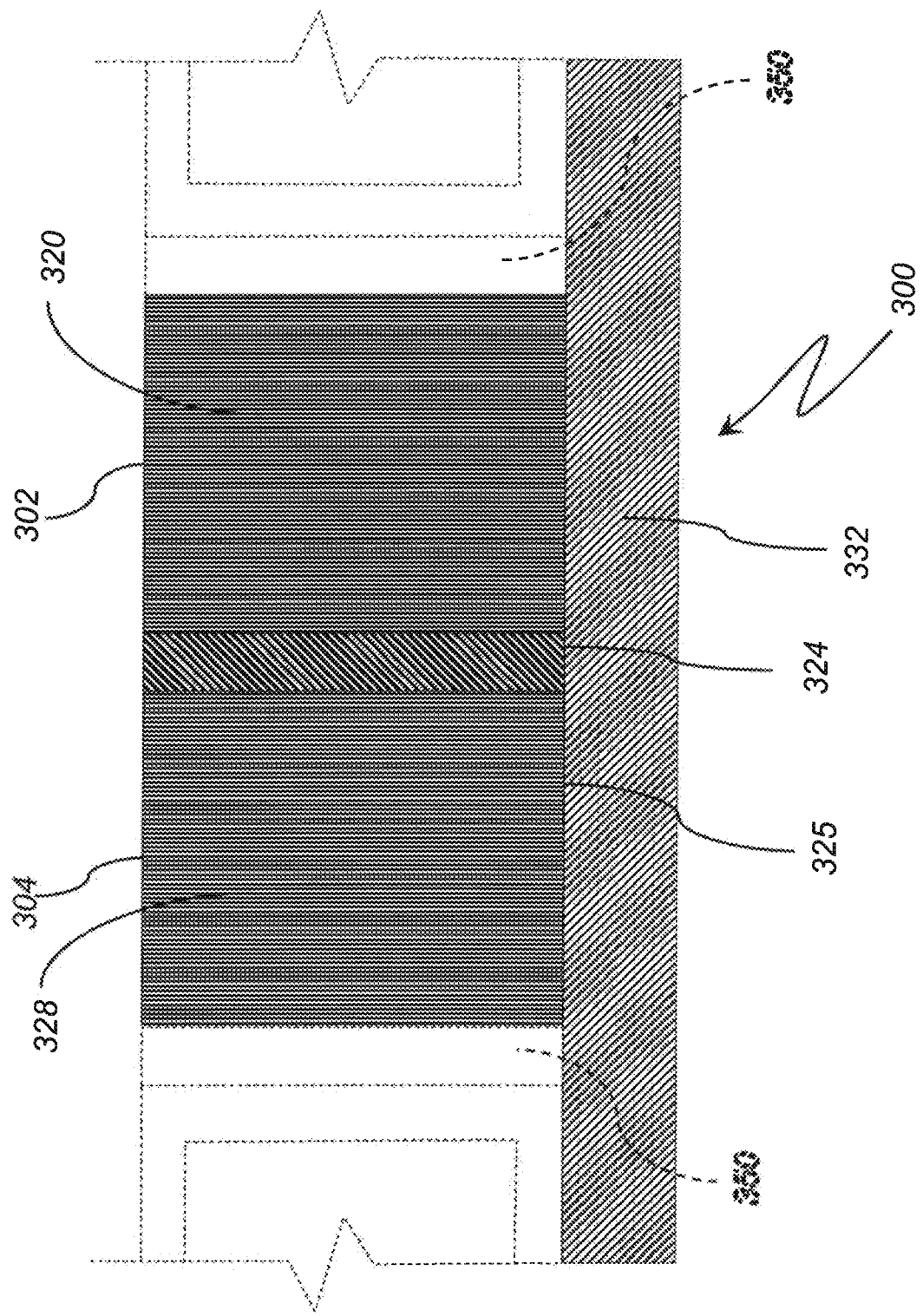
FIG. 6 is a cross-sectional view of the electrolytic ozone generator of FIG. 3, showing the electrode pairs fixed to the external support structure.

With reference to FIG. 6, electrolytic ozone generator 300 is shown according to an externally supported embodiment. In this respect electrolytic ozone generator 300 has an external support 332. External support 332 has a deposition surface 325. Anode 302 and cathode 304 are integrally fixed to deposition surface 325, anode material 320 and cathode material 328 each being deposited aver deposition surface 325 to define anode 302 and cathode 304. In embodiments having anodes and cathodes formed of a common material, e.g., anode 302 and cathode 304, an isolator gap 324 is defined within the common material to separate anode 302 from cathode 304. Isolator 106 is arranged within isolator gap 324.

As will be appreciated by those of skill in the art in view of the present disclosure, use of external support 132 facilitates scaling electrolytic ozone generator 100 for a desired application by allowing tailoring of the amount of active area (i.e., aggregate length of anode longitudinal edge 114 and cathode longitudinal edge 116 included in electrolytic ozone generator 100, as will be described) incorporated in a given electrolytic ozone generator 100 by dicing the substrate wafer as appropriate for a contemplated application. In certain embodiments external support 132 can include silicon oxide, external support being a segment of a silicon oxide wafer.

Figure 7:
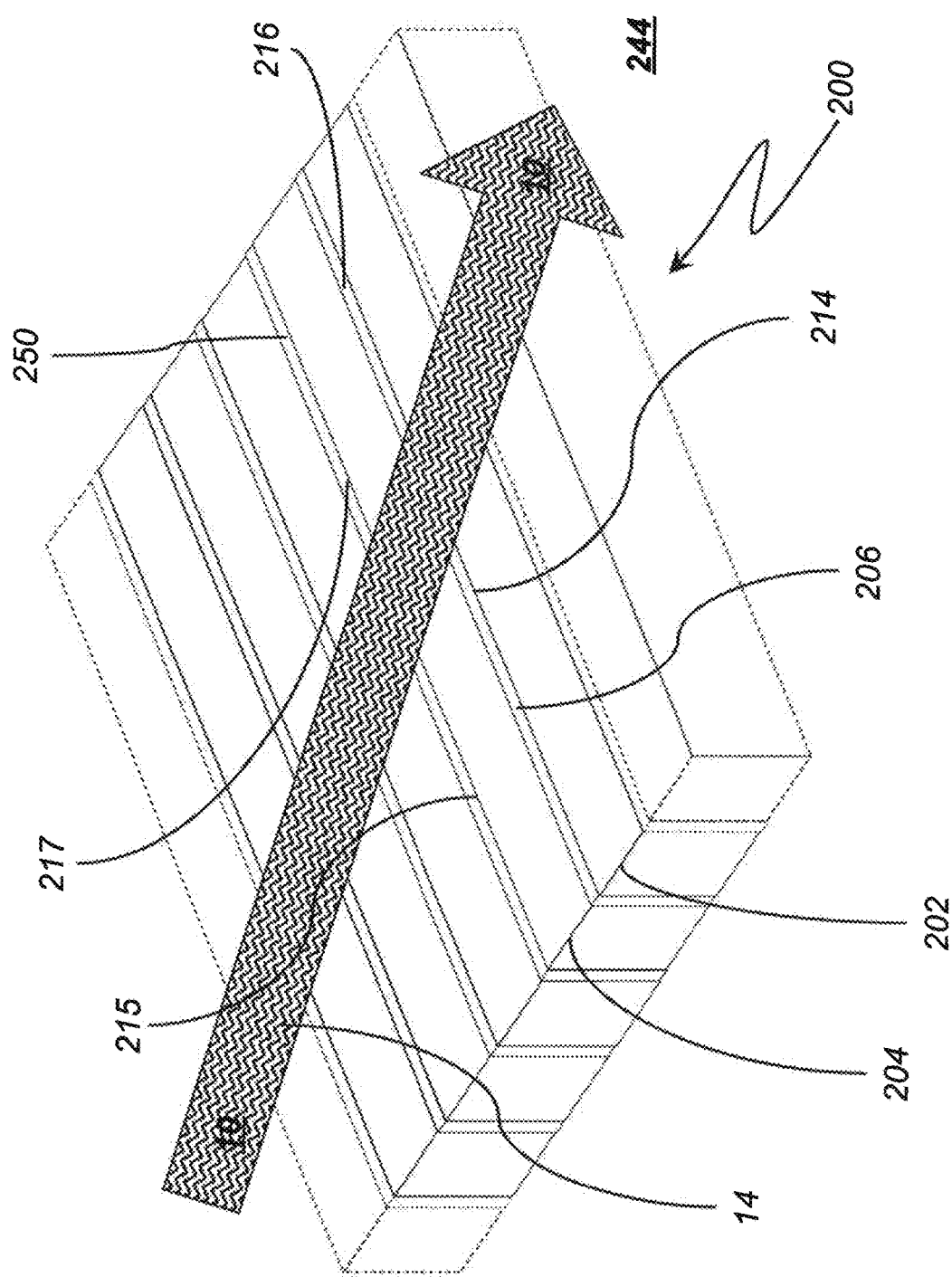
FIG. 7 is perspective view of the electrolytic ozone generator of FIG. 2, showing longitudinal edges of the anode and cathode in fluid communication within a common space.

With reference to FIG. 7, flow 14 of water 10 across electrolytic ozone generator 200 is shown. Flow 14 traverses electrolytic ozone generator 200 within a flow area 244. Flow area 244 fluidly couples longitudinal edges of the electrode pairs forming ozone generator 200. In this respect longitudinal edge 214 of anode 202 is in fluid communication with longitudinal edge 216 of cathode 204, flow 14 spanning isolator 206. Flow area 244 also fluidly couples longitudinal edge 215 of cathode 204 with longitudinal edge of the anode of the adjacent electrode pair, spanning intermediate isolator 250.

Since ozone gas arises in the flow area 244 adjacent to the longitudinal edges of the anodes and cathodes, and flow 14 is otherwise unconstrained by the structure of electrolytic ozone generator 200, the direction of flow 14 can be selected independently of the orientation of flow 14 relative to longitudinal edges of the anode and cathodes of electrolytic ozone generator 200. For example, in the illustrated exemplary embodiment flow 14 is oblique relative to the longitudinal edges of the anodes and cathodes. This is for illustration purposes only and is non-limiting. It is contemplated that flow 14 can be orthogonal or parallel to the longitudinal edges of the anode and cathodes of electrolytic ozone generator, as suitable for an intended application.

Figure 8:
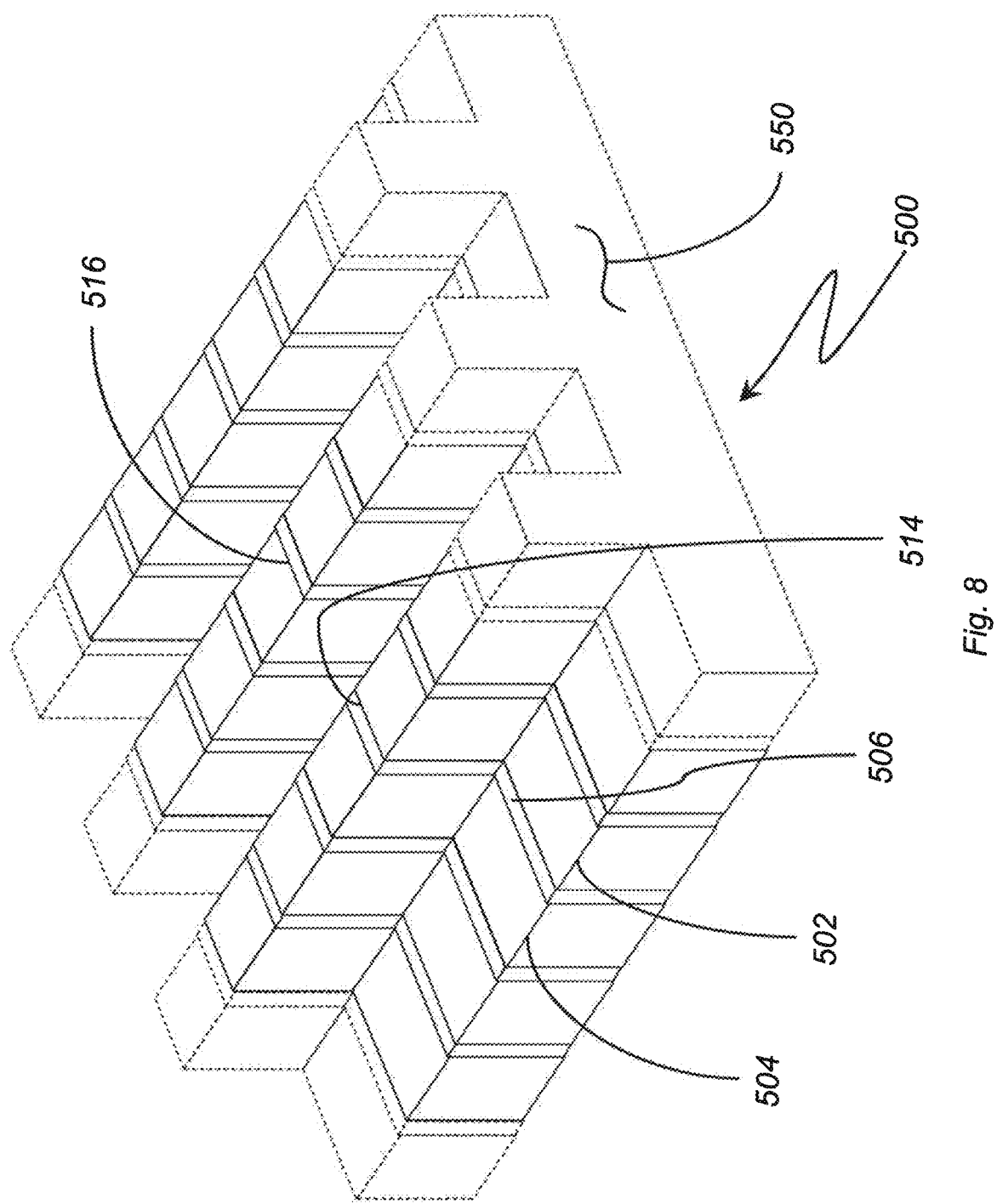
FIG. 8 is a perspective view of an electrolytic ozone generator having a non-linear profile, showing the increased active area formed by the longitudinal edges of the anodes and cathodes.

With reference to FIG. 8, an electrolytic ozone generator 500 is shown. Electrolytic ozone generator 500 is similar to electrolytic ozone generator 100 (shown in FIG. 1) and additionally includes an anode 502, a cathode 504, and an isolator 506 having a non-linear profile 550. Non-linear profile 550 provides an anode longitudinal edge 514 and cathode longitudinal edge 516 that are each longer than the longitudinal length of anode 502 and cathode 504. In the illustrated exemplary embodiment non-linear profile 550 is shown as a stepped profile having orthogonal intersecting surfaces. This is for illustration purposes only and is non-limited. As will be appreciated by those of skill in the art in view of the present disclosure non-linear profile 550 can be arcuate and/or irregular, as suitable for an intended application.

As will also be appreciated by those of skill in the art in view of the present disclosure, increasing the longitudinal length of anode and cathode longitudinal edges with respect to the longitudinal lengths of the anode and cathode increases the rate of ozone generation from electrolytic ozone generator 500 without impacting the mechanical stability (or robustness) or electrolytic ozone generator 500. Although a stepped profile 550 is shown in FIG. 8, those of skill in the art will recognize that other profile shapes can be employed to increase the length of the longitudinal edges of the anode and cathode in relation to the longitudinal lengths of the anode and cathode, as suitable for an intended application.

Figure 9:
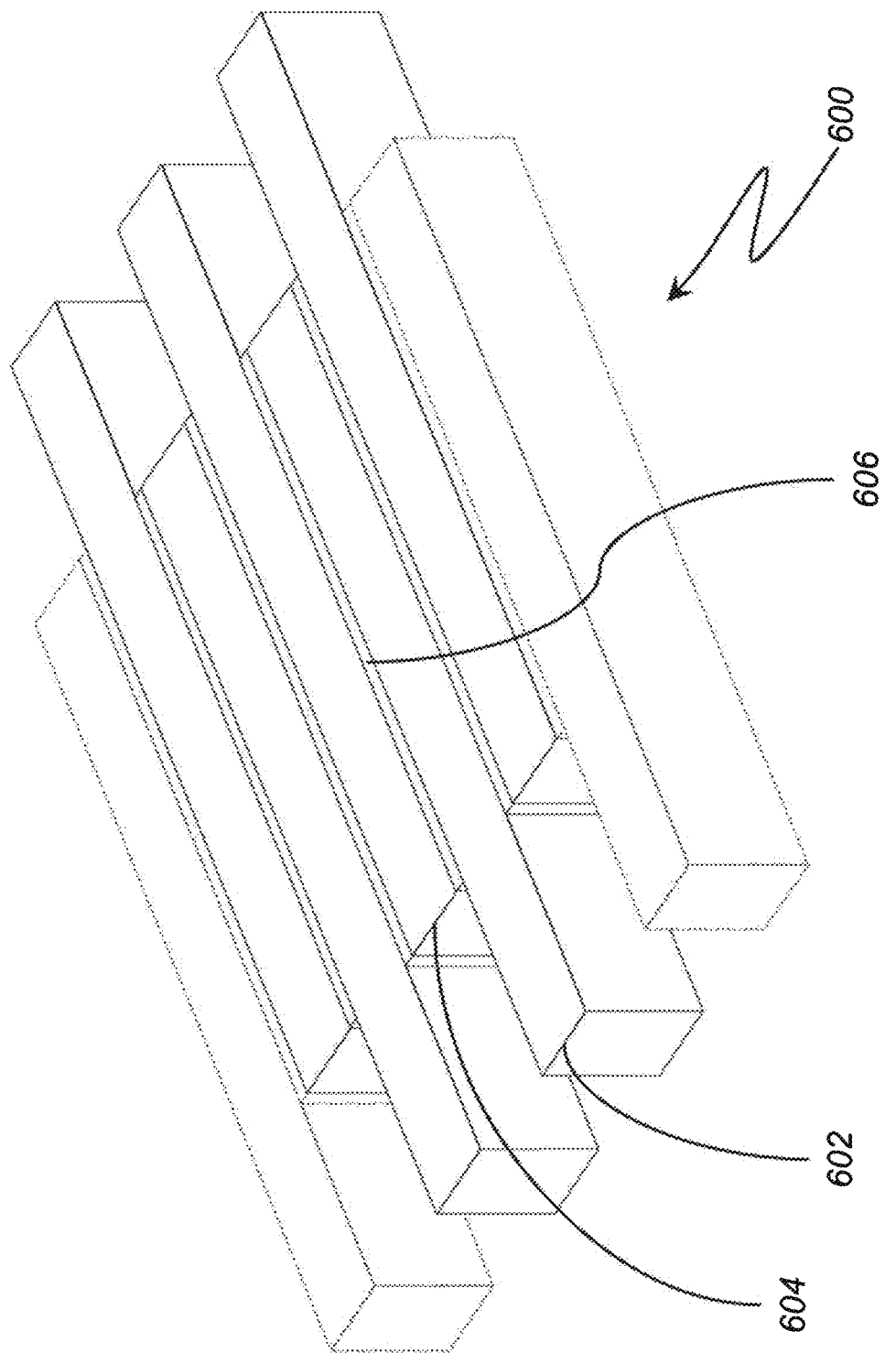
FIG. 9 is a perspective view of an electrolytic ozone generator having an anode and a cathode in a longitudinally staggered arrangement.

With reference to FIG. 9, an electrolytic ozone generator 600 is shown. Electrolytic ozone generator 600 is similar to electrolytic ozone generator 100 (shown in FIG. 1) and additionally includes an anode 602 and a cathode 604 separated by an isolator 606. Cathode 604 is longitudinally staggered with respect to anode 602. Staggering cathode 604 longitudinally relative to anode 602 offsets the ends of anode 602 relative to cathode 604. This simplifies electrical connection of the anodes, e.g., anode 602, and cathodes, e.g., cathode 604, of electrolytic ozone generator 600 as a positive lead can connect to each of the anodes while spanning the intervening cathode along a straight path. A negative lead similarly connecting to each of the cathodes and spanning each of the anodes can similarly be arranged on the longitudinally opposite end of electrolytic ozone generator 600.

Figure 10:
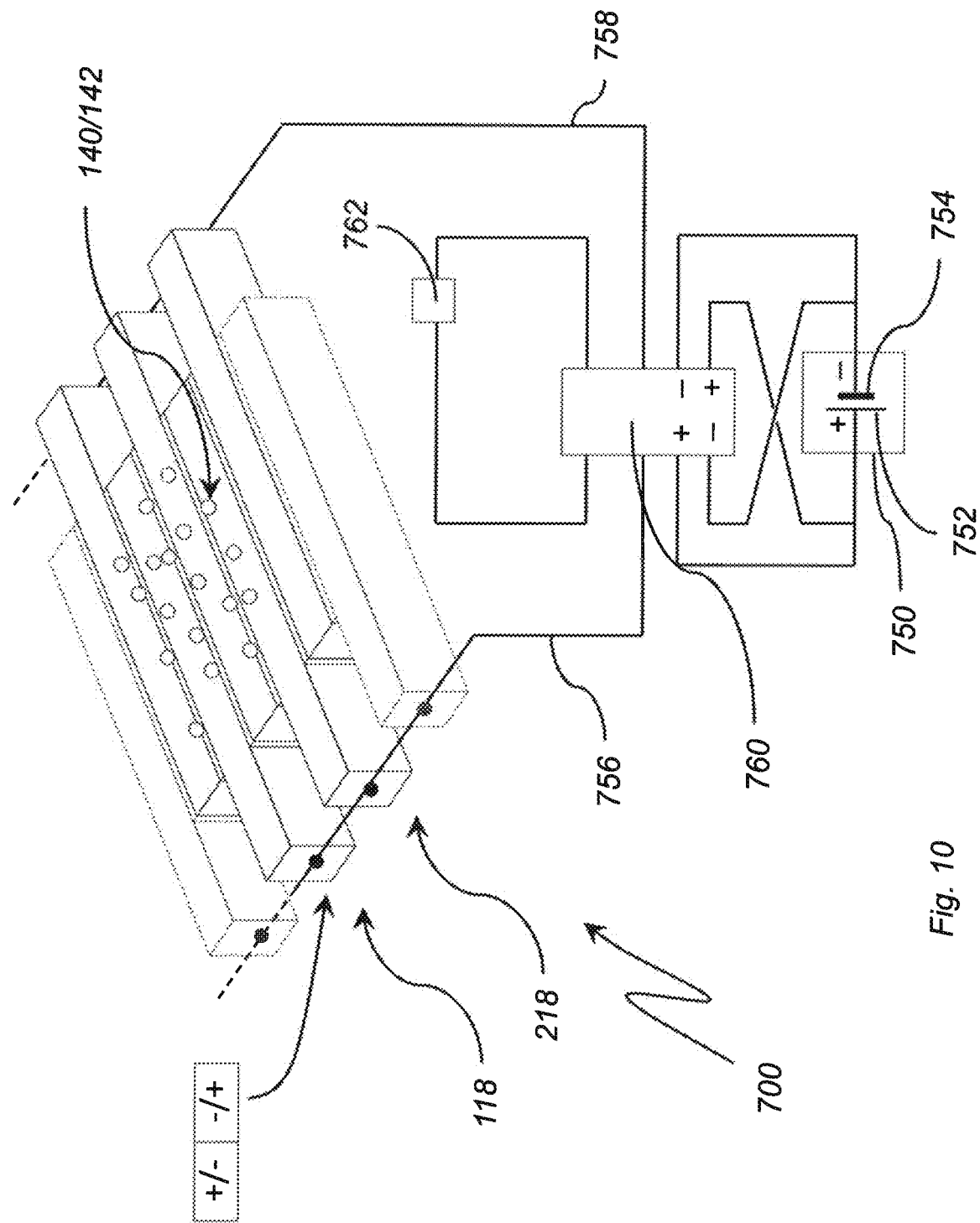
FIG. 10 is a perspective view of the electrolytic ozone generator of FIG. 9, showing positive and negative leads connected to longitudinally opposite ends of the longitudinally offset anodes and cathodes.

With reference to FIG. 10, an electrolytic ozone generator 700 is shown. Electrolytic ozone generator 700 is similar to electrolytic ozone generator 600 (shown in FIG. 9) and additionally includes a first electrode pair 118, a second electrode pair 218, and a power source 750. Power source 750 includes a positive terminal 752 and negative terminal 754. A positive lead 756 electrically connects positive terminal 752 of power source 750 with each of the anodes of electrolytic ozone generator 700, e.g., the anodes of first electrode pair 118 and second electrode pair 218. A negative lead 758 electrically connects negative terminal 754 of power source 750 with cathodes of electrolytic ozone generator 700, e.g., the cathodes of first electrode pair 118 and second electrode pair 218. It is contemplated that power source 750 be arranged to apply a potential difference across the anodes and cathodes of electrolytic ozone generator 700 sufficient to generate ozone gas 142 from water 10 (shown in FIG. 7), as described above.

In the illustrated exemplary embodiment, electrolytic ozone generator 700 also includes a polarity-reversing module 760 and a frequency-varying module 762. Polarity-reversing module 760 is connected between positive lead 756 and negative lead 758, power source 750 being arranged to reverse the polarity of voltage applied to the anodes and cathodes of electrolytic ozone generator 700.

Frequency-varying module 762 is operatively connected to the polarity reversing module 760. It is contemplated that frequency-varying module 762 be arranged to vary the frequency of polarity change of voltage applied to the anodes and cathodes of electrolytic ozone generator 700.

As will be appreciated by those of skill in art in view of the present disclosure, reversing polarity can be advantageous to manage scale production with electrolytic ozone generator 700. For example, when water 10 (shown in FIG. 7) contains alkaline earth metals, which can precipitate as insoluble minerals (scale) along the longitudinal edges of the cathodes in the presence of the hydroxyl anions (OH⁻), compounds like $Mg(H)_2$ and $CaCO_3$ can form at the longitudinal edge of the cathode per reaction (4) (shown above).

Reversing the polarity of voltage applied to electrolytic ozone generator 700, i.e. by applying a negative charge to the anode and applying a positive charge to the cathode, causes the longitudinal edges of the cathodes to function as anodes. This produces protons (H⁺) locally, i.e., in proximity to the longitudinal edges of the cathodes, which lower the local pH in proximity of the longitudinal edge of the anode, causing the scale to re-dissolving into water 10 (shown in FIG. 7). Scale removal in turn improves the reliability of electrolytic ozone generator 700—without reducing ozone water output.

With reference to FIGS. 11a and 11b, an ozone water apparatus 800 is shown. Ozone water apparatus 800 includes a water conduit 804. Water conduit 804 has an interior surface 802 at partially bounding flow path 14, water 10 thereby flowing through water conduit 804. As shown in FIG. 11b, a plurality of electrolytic ozone generators 100 are arranged within water conduit 804 and fixed therein to interior surface 802. Being fixed to interior surface 802, longitudinal edges, e.g., longitudinal edge 114 and longitudinal edge 116, are in fluid communication with one another within flow 14—flow 14 defining a common space traversing the longitudinal edges to take ozone generated in the active areas of electrolytic ozone generator 100.

In the illustrated exemplary embodiment a common space is located on a single side of electrolytic ozone generator 100 fluidly couples longitudinal edge 114 of anode 102 (shown in FIG. 1) to longitudinal edge 116 of the cathode 104 (shown in FIG. 1), ozone water generator 800 thereby scaling by adding additional electrolytic ozone generators 100 to interior surface 802 of water conduit 804. As will the appreciated by those of skill in the art, water flow, i.e., flow 14, through the common space causes flow 14 to sweep ozone gas into water 10, facilitating take-up of dissolved ozone gas into water 10 and continuously renewing makeup water at the active areas of the electrolytic ozone generators 100. This facilitates relatively high ozone output and take-up in relation to ozone generators requiring makeup water to flow through a membrane and/or anode and cathode structures.

With reference to FIG. 11c, an ozone water apparatus 900 is shown. Ozone water apparatus 900 is similar to ozone water apparatus 800 (shown in FIG. 11a), and additionally includes electrolytic ozone generators 100 arranged within the flow area of a water conduit 904. More particularly, ozone water generators 100 are fixed an interior surface 902 of water conduit 904 such that water 10 flowing through water conduit 904 traverses both surfaces of the respective ozone water generators 100, increasing ozone output from ozone water generators 100. As will be appreciated by those of skill in the art in view of the present disclosure, the illustrated arrangement demonstrates scalability by fluidly coupling longitudinal edges of the anode and cathode on common areas on opposite sides of the electrolytic ozone generator.

Figure 13:
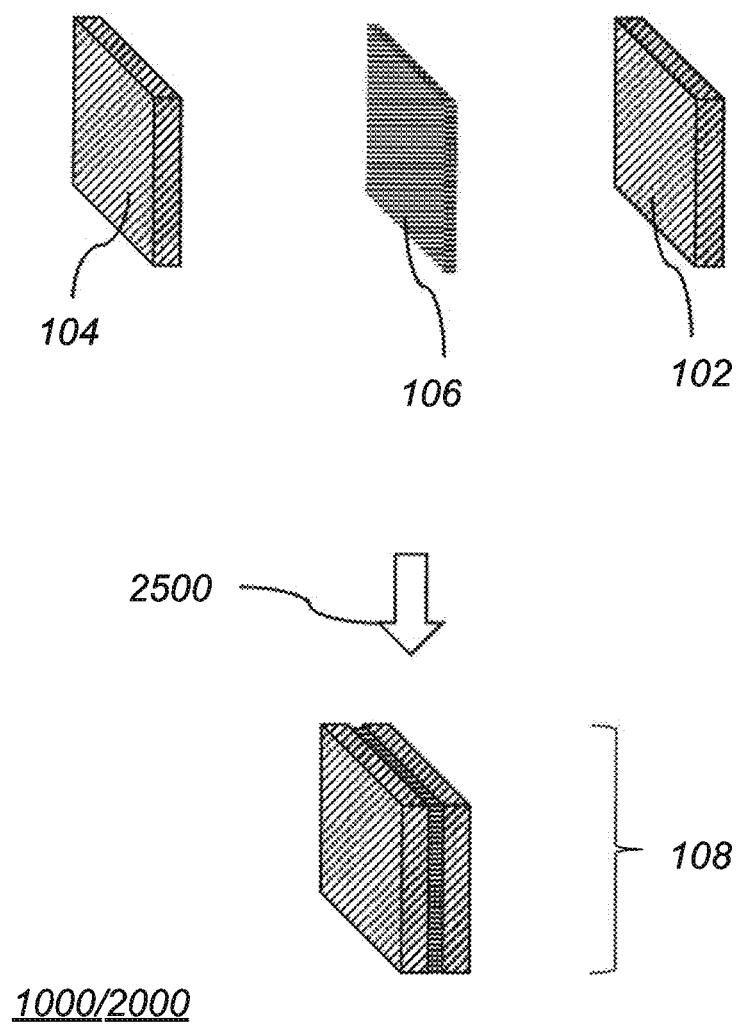
FIG. 13 is a diagram of operations for assembling the anodes and cathodes of FIGS. 12a and 12b, showing assembly of the anode and cathode with an isolator.

With reference to FIGS. 12a and 13, a method 1000 making a self-supporting electrolytic ozone generator, e.g., electrolytic ozone generator 100 (shown in FIG. 1), is shown. Method 1000 includes depositing 1100 an electrode material on a substrate. A portion of the electrode is removed in a removal operation 1200, such as in an etching operation, separating the electrode material into an anode and a cathode formed of a common electrode material. In the illustrated exemplary embodiment the substrate is then removed in a substrate removal operation 1300, thereby forming discrete and self-supporting anodes and cathodes. The anode and cathode are then coupled to one another by an isolator, e.g., isolator 106 (shown in FIG. 1), in a coupling operation 2500 (shown in FIG. 13), and the electrolytic ozone generator is then fixed within a water conduit and connected electrically to a power source for generating ozone. It is contemplated that electrolytic ozone generator 100 can be fabricated using microfabrication techniques and semiconductor manufacturing process. This allows for manufacture of electrolytic ozone generators, e.g., electrolytic ozone generator 100, in volume.

With reference to FIGS. 12b and 13, a method 2000 making an internally supported electrolytic ozone generator, e.g., electrolytic ozone generator 100 (shown in FIG. 1), is shown. Method 2000 includes depositing 2100 an electrode material on an anode internal support and a cathode internal support. The electrode material is deposited on at least two surfaces of the support such that the substrate is arranged internally and the anode, e.g., anode 102, is coupled to the cathode, e.g., cathode 104 by an isolator, e.g., isolator 106, is a coupling operation 2500 (shown in FIG. 13). The electrolytic ozone generator is then fixed within a water conduit and connected electrically to a power source for generating ozone.

Figure 14:
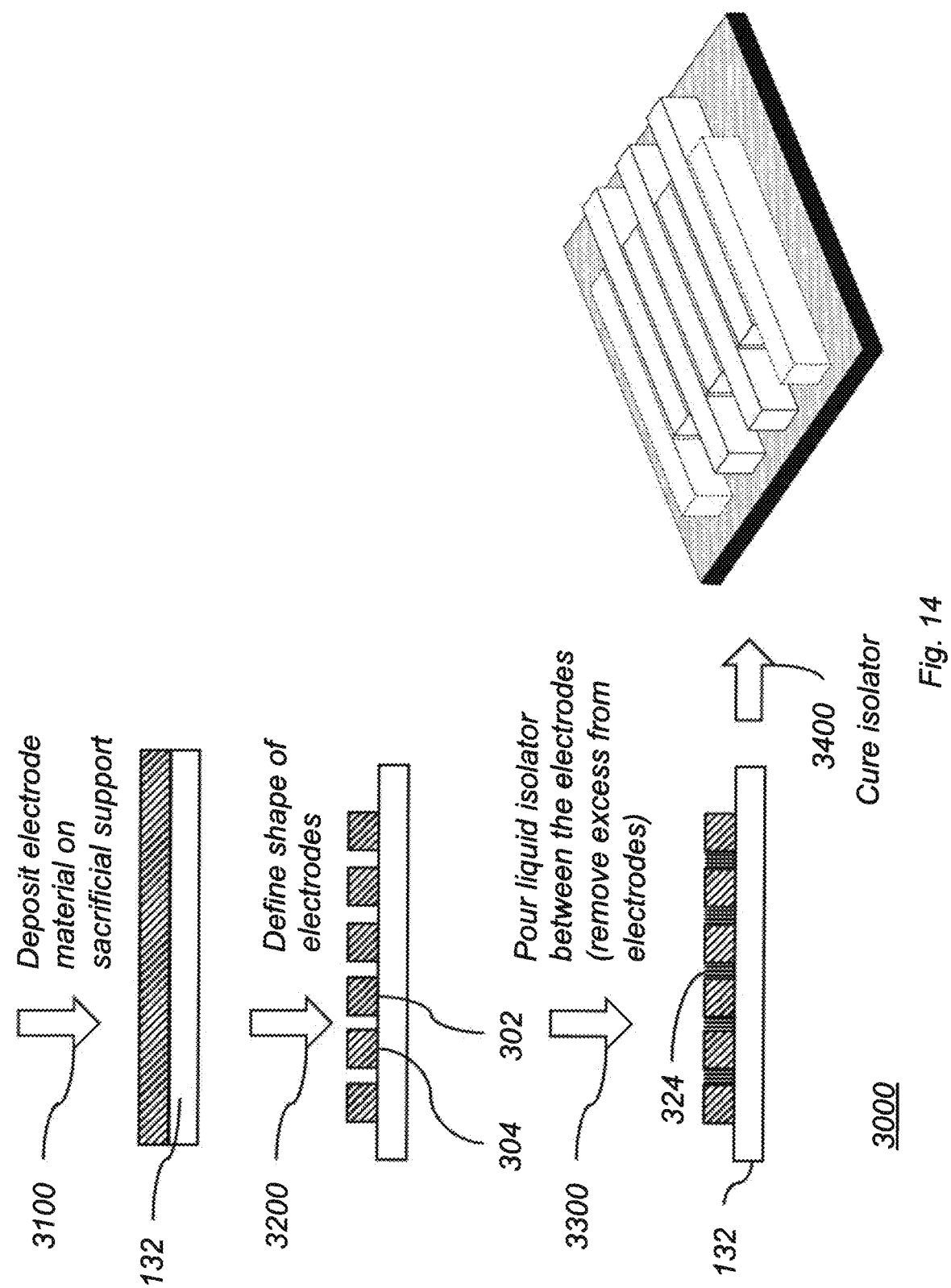
FIG. 14 is a diagram of a method of making an externally supported electrolytic ozone generator, showing an anode and cathode being fabricated on an external support.

With reference to FIG. 14, a method 3000 of making an externally-supported electrolytic ozone generator, e.g., electrolytic ozone generator 300, is shown. Method 3000 includes depositing an electrode material on an external insulating substrate in a deposition operation 3100. Anodes and cathodes are then defined on the substrate in situ on the substrate in a removal operation 3200, defining isolator gaps between the respective anodes and cathodes. The isolator gaps are then filled in an isolator deposition operation 3300, the isolators separating anodes and cathodes of electrode pairs and anodes and/or cathodes of adjacent electrode pairs. The substrate remains connected to the anodes and cathodes as an external support, providing electrical separation between anodes and cathodes of the electrolytic ozone generator. As above, the electrolytic ozone generator is then fixed within a water conduit and connected electrically to a power source for generating ozone.

Example 1

A first exemplary electrolytic ozone generator was constructed according to the arrangement of electrolytic ozone generator 200 (shown in FIG. 2). The first exemplary embodiment included internal support structures, e.g., support structure 128 (shown in FIG. 5), in each anode and cathode. The first exemplary electrolytic ozone generator also had three electrode pairs, e.g., electrode pair 118 (shown in FIG. 4), respective electrode pairs being separated by intermediate isolators 250, e.g., intermediate isolator 250 (shown in FIG. 2), resulting in five (5) ozone-producing longitudinal edges.

Each anode and cathode was fabricated by (a) forming supports, (b) depositing a common material on the support to form anode material 120 (shown in FIG. 4) and cathode material 122 (shown in FIG. 4), and (c) connecting the anode pairs 118 to power source, e.g., power source 550 (shown in FIG. 10). The supports were cut from a p-type silicon wafer and were dimensioned to be about 4 centimeters long, having a width of about 1 centimeter, and be about 300 microns high.

The supports were placed in an HF-CVD reactor for to deposit the common anode and cathode material. In the first exemplary electrolytic ozone generator the common material was BDD. The BDD was deposited on all sides, absent the long face contacting the HF-CVD reactor floor, and in a thickness of about 2 microns. Cathodes and anodes were then designated from among the otherwise identical structures as electrode pairs, and the anode/cathodes of each electrode pair coupled to one another by fabrication an isolator, e.g., isolator 106 (shown in FIG. 1). The electrode pairs where coupled to one another of intermediate isolators, e.g., intermediate isolator 250 (shown in FIG. 5), and the assembly connected to the power source.

Figure 15:
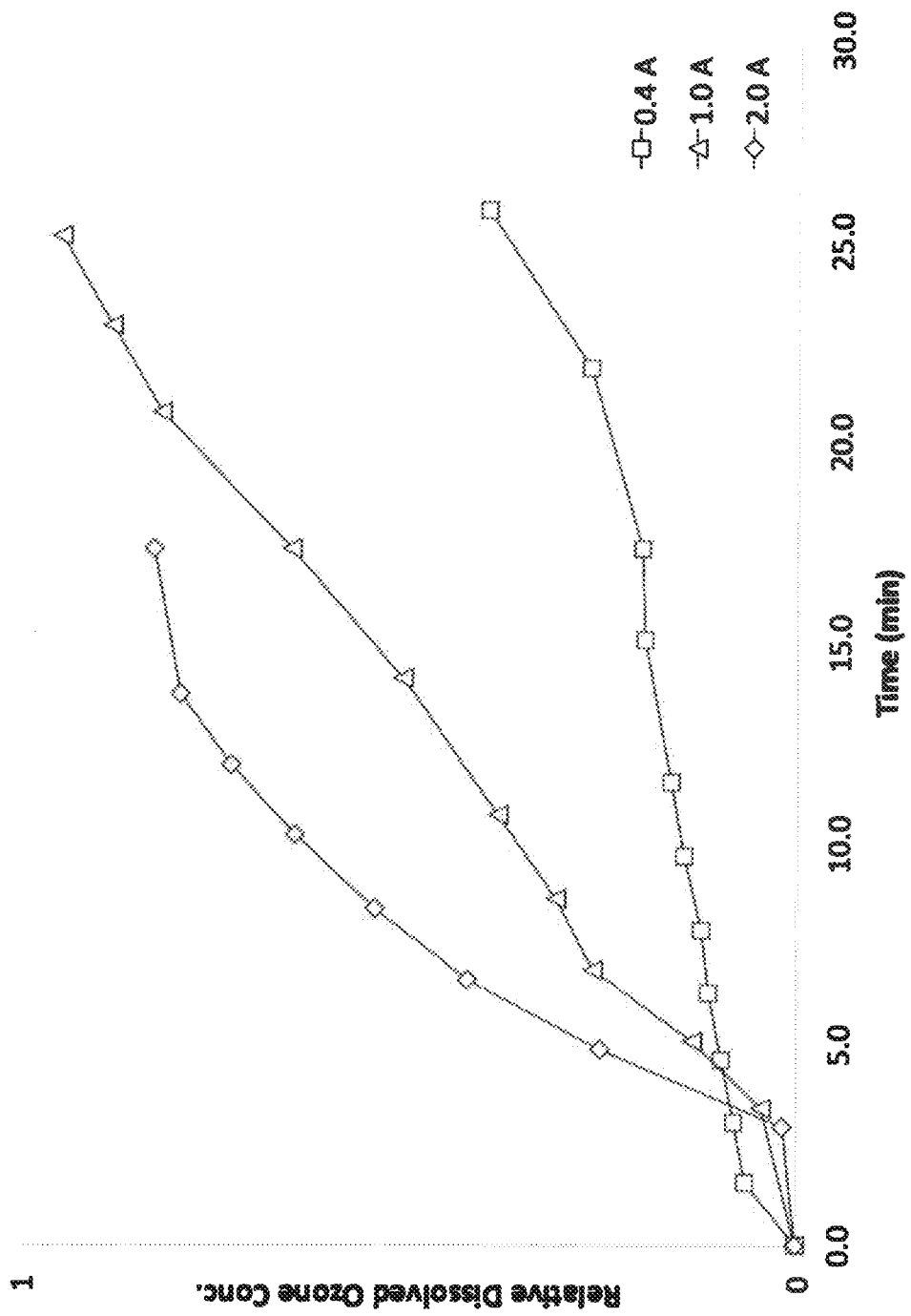
FIG. 15 is a graph illustrating operation of an exemplary electrolytic ozone generator constructed according to the present disclosure, showing dissolved ozone concentration as a function of time at different current flows.

Two tests were performed. First, a static ozone production in a finite water volume and with running water at different flow rates and currents test was performed. Regular tap water was used to test the device. The device was placed in a finite volume of regular tap water. As shown in FIG. 15, ozone concentration was measured at different time intervals and at different applied currents. The test electrolytic ozone generator demonstrated an ozone concentration increases over time as expected given the continuous generation of ozone of the device. Surprisingly, the electrolytic ozone generator demonstrated a rate of increase in ozone concentration proportional to the applied current, indicating that the electrolytic ozone generator creates ozone from the applied current, as it was expected from an electrolytic process. At relatively high current, a peak ozone generation rate was identified, driven by heating of the finite volume of water used for ozone generation, demonstrating that the exemplary electrolytic ozone generator was operating in accordance with equation (1)-(5).

Figure 16:
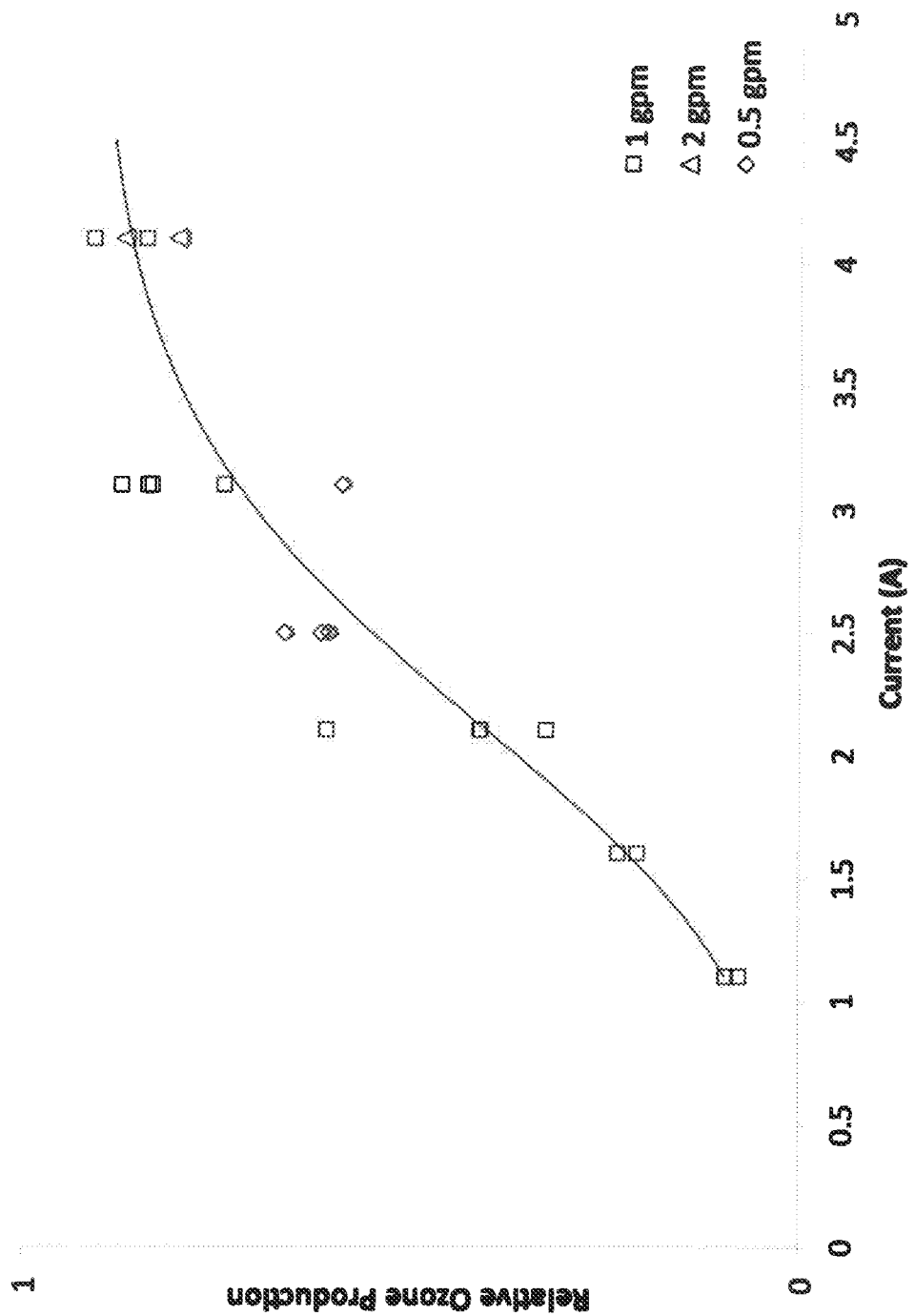
FIG. 16 is a graph illustrating operation of another exemplary electrolytic ozone generator constructed according to the present disclosure, showing normalized ozone production at different current flows and water flow rates.
Figure 17:
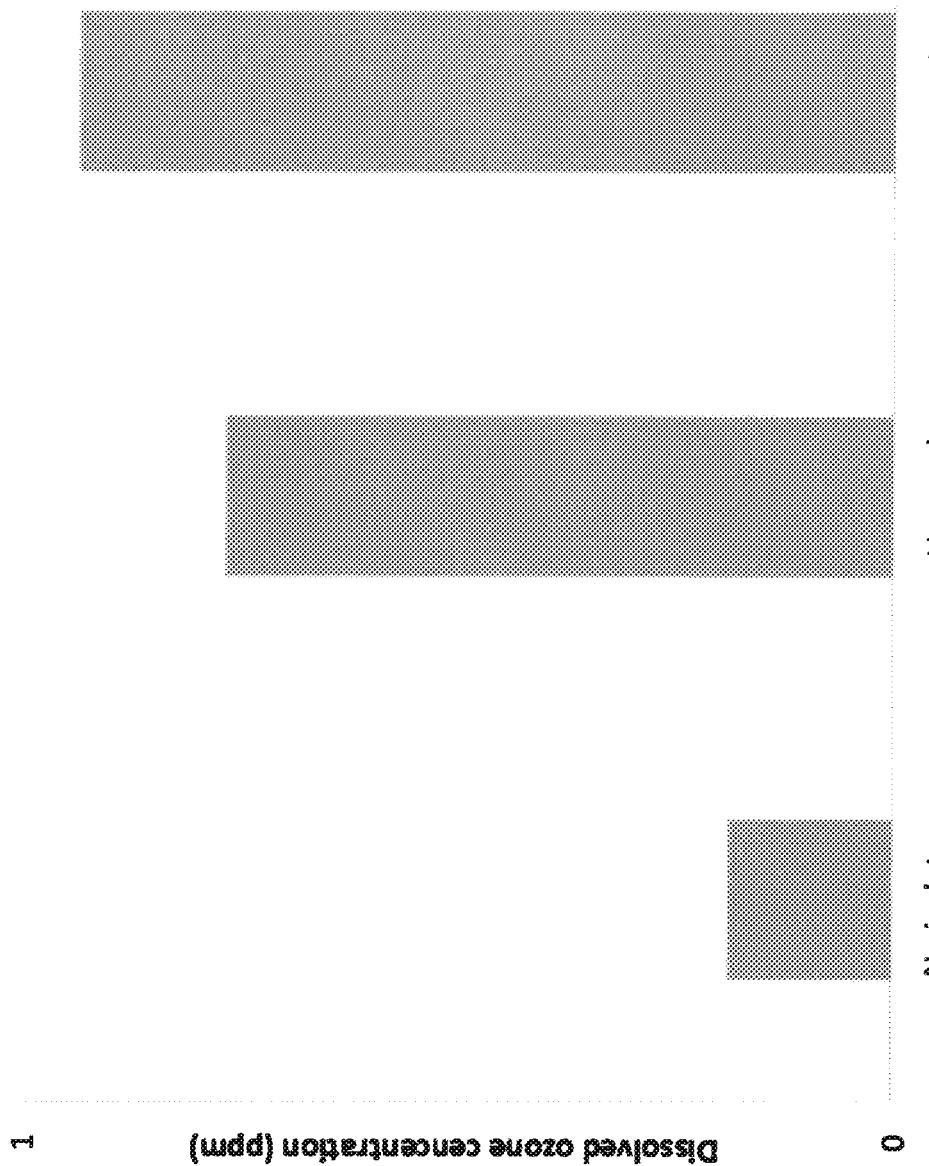
FIG. 17 is a graph illustrating operation of yet another exemplary electrolytic ozone generator constructed according to the present disclosure, showing dissolved ozone concentration for electrolytic ozone generators having no isolator, uncured isolators, and cured isolators.

Second, the electrolytic ozone generator was placed inside a rubber tube in order to flow water at specific flow rates. As shown in FIG. 16, the electrolytic ozone generator demonstrated an ozone production rate increase corresponding to current increase and independent of the water flow rate. This is an indication that the water flow does not affect the performance of the electrolytic ozone generator. This is in marked contrast to electrolytic ozone generators where water traverses holes, the flow rate of the water over the electrodes can have a significant impact on the performance of the device since the turbulence of the water can affect the removal of the gas from the holes as well as promote the hydration of the membrane. In contrast, the electrolytic ozone generator of the present disclosure gas formation and membrane hydration are significantly less impacted by the turbulence effect of the water.

Example 2

A second exemplary electrolytic ozone generator was constructed according to the arrangement of electrolytic ozone generator 300 (shown in FIGS. 3, 6 and 14). The second exemplary embodiment included an external support structures, e.g., support structure 132 (shown in FIGS. 3 and 4), underling each anode and cathode of the apparatus. The second exemplary electrolytic ozone generator also had dozens of electrode pairs, e.g., electrode pair 118 (shown in FIG. 2), respective electrode pairs separated by intermediate isolators 250, e.g., intermediate isolator 250 (shown in FIG. 5).

More particularly, the second exemplary electrolytic ozone generator was fabricated over a silicon oxide wafer. The silicon oxide wafer received an HF-CVD reactor deposition of BDD over the silicon oxide wafer. Standard microfabrication processes then utilized to form the anode, cathode, and electrical connections generated the electrodes and electrical connections shown in FIG. 10. In this case the anode material and the cathode material include only the BDD The isolator was formed from Nafion between the anode and the cathode was fabricated by curing a liquid Nafion dispersion (D520). Specifically, the Nafion dispersion was cast over the electrodes and then cured on a hotplate for several hours. Subsequently, the excess Nafion over the electrodes was removed with a razor blade in order to expose the electrode-membrane interfaces, in which the electrolytic reactions occur.

The second exemplary electrolytic ozone generator was then tested in a finite water volume. Notably, little ozone generation occurred at locations stripped of Nafion between the anode and cathode, whereas the electrolytic ozone generator generated significant amounts of ozone in proximity to the Nafion dispersion, either cured or not, but mostly cured. Because of the greater mechanical stability of the cured Nafion, it is contemplated that cured Nafion be incorporated in isolator 106.

The methods and systems of the present disclosure, as described above and shown in the drawings, provide for electrolytic ozone generators and methods of making electrolytic ozone generators with superior properties including ease of manufacture, scalability, and robustness. While the apparatus and methods of the subject disclosure have been shown and described with reference to preferred embodiments, those skilled in the art will readily appreciate that change and/or modifications may be made thereto without departing from the scope of the subject disclosure.

What is claimed is:

1. An electrolytic ozone generator, comprising a plurality of electrode pairs, each electrode pair containing:
    an anode with a longitudinal edge;
    a cathode with a longitudinal edge; and
    an isolator comprising a proton-exchange membrane in contact with and electrically separating the cathode from the anode, the longitudinal edges provide a contact with the isolator so that water in a common water flow area fluidly couples the longitudinal edge of the anode with the longitudinal edge of the cathode without flowing water through the anode, the cathode, and the isolator, and an intermediate isolator comprising a proton-exchange membrane being arranged between the anode and the cathode of an adjacent electrode pair, wherein the longitudinal edge of the anode is opposite to the longitudinal edge of the cathode.

2. The electrolytic ozone generator as recited in claim 1, wherein the cathode and the anode include a common material.

3. The electrolytic ozone generator as recited in claim 1, wherein the cathode and the anode each include diamond.

4. The electrolytic ozone generator as recited in claim 1, wherein the cathode and the anode each include at least one of boron-doped diamond, nitrogen-doped diamond, and phosphorus-doped diamond.

5. The electrolytic ozone generator as recited in claim 1, wherein the anode and cathode further comprising a support.

6. The electrolytic ozone generator as recited in claim 5, wherein the support is an internal support and a material forming the anode is deposited over the internal support and a material forming the cathode is deposited over the internal support.

7. The electrolytic ozone generator as recited in claim 5, wherein the support is an external support, the anode and the cathode being coupled to a common surface of the external support.

8. The electrolytic ozone generator as recited in claim 1, wherein the longitudinal edge of the anode has a length that is greater than a longitudinal length of the anode.

9. The electrolytic ozone generator as recited in claim 1, wherein the anode and the cathode have a non-linear profile.

10. The electrolytic ozone generator as recited in claim 1, wherein the anode is longitudinally staggered relative to the cathode.

11. The electrolytic ozone generator as recited in claim 1, wherein the electrolytic ozone generator is seated against an internal surface of a water conduit, the common water flow area of the water conduit fluidly coupling the anode longitudinal edge with the cathode longitudinal edge.

12. The electrolytic ozone generator as recited in claim 1, further comprising a power source with a positive lead connected to the anode and a negative lead connected to the cathode, wherein the power source is a reversing polarity power source with variable frequency of reversing polarity connected to the anode and the cathode through the positive lead and the negative lead.

13. The electrolytic ozone generator as recited in claim 1, wherein at least one of the anode and the cathode has an arcuate profile.

14. An ozone water generator, comprising:
a water conduit defining water flow area; and
an electrolytic ozone generator as recited in claim 1, wherein the electrolytic ozone generator is fixed to an interior surface of the water conduit such that the water flow area is fluidly coupled the longitudinal edge of the anode to the longitudinal edge of the cathode in a common space.

15. The ozone water generator as recited in claim 14, wherein the common space is located on a single side of the electrolytic ozone generator.

16. The ozone water generator as recited in claim 14, wherein the common space is a first common space, and wherein the flow area fluidly couples the longitudinal edge of the anode to the longitudinal edge of the cathode in a second common space on a side of the electrolytic ozone generator opposite the first common space.

\* \* \* \* \*